(12) United States Patent
Matzinger

(10) Patent No.: US 8,475,733 B2
(45) Date of Patent: *Jul. 2, 2013

(54) HAND-HELD TEST METER AND ANALYTICAL TEST STRIP CARTRIDGE ASSEMBLY WITH DESICCANT VIAL

(75) Inventor: David Matzinger, Menlo Park, CA (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,450

(22) Filed: May 4, 2012

(65) Prior Publication Data

US 2013/0034872 A1 Feb. 7, 2013

Related U.S. Application Data

(63) Continuation-in-part of application No. 13/198,536, filed on Aug. 4, 2011.

(51) Int. Cl.
*B01L 9/06* (2006.01)
*A61B 5/00* (2006.01)
*C12M 1/34* (2006.01)

(52) U.S. Cl.
USPC ............... 422/404; 600/300; 435/287.1

(58) Field of Classification Search
USPC ............................................. 422/404
See application file for complete search history.

(56) References Cited

U.S. PATENT DOCUMENTS

| | | | |
|---|---|---|---|
| 5,510,266 A | 4/1996 | Bonner et al. | |
| 5,575,403 A | 11/1996 | Charlton et al. | |
| 5,708,247 A | 1/1998 | McAleer et al. | |
| 5,720,924 A | 2/1998 | Eikmeier et al. | |
| 5,951,836 A | 9/1999 | McAleer et al. | |
| 6,241,862 B1 | 6/2001 | McAleer et al. | |
| 6,284,125 B1 | 9/2001 | Hodges et al. | |
| 6,881,578 B2 | 4/2005 | Otake | |
| 7,172,728 B2 * | 2/2007 | Otake | 422/404 |
| 7,468,125 B2 | 12/2008 | Kraft et al. | |
| 7,661,325 B2 | 2/2010 | Nishina | |
| 2002/0076349 A1 | 6/2002 | Aitken et al. | |
| 2003/0002387 A1 | 1/2003 | Bottwein et al. | |
| 2003/0191415 A1 * | 10/2003 | Moerman et al. | 600/584 |
| 2003/0212345 A1 * | 11/2003 | McAllister et al. | 600/584 |
| 2005/0143675 A1 * | 6/2005 | Neel et al. | 600/583 |
| 2005/0240119 A1 * | 10/2005 | Draudt et al. | 600/583 |

(Continued)

FOREIGN PATENT DOCUMENTS

| | | |
|---|---|---|
| EP | 1321769 B1 | 7/2006 |
| EP | 1726950 A1 | 11/2006 |
| EP | 1967851 A1 | 9/2008 |
| WO | WO 2006/059232 A1 | 6/2006 |

*Primary Examiner* — Jill Warden
*Assistant Examiner* — Brittany Fisher

(57) ABSTRACT

A hand-held test meter and analytical test strip cartridge assembly combination includes a hand-held test meter with a test meter housing and an extractor with a test strip engagement feature, while the analytical test strip cartridge assembly includes a desiccant vial and an analytical test strip cartridge with a cartridge housing, a test strip presentation mechanism disposed within the cartridge housing, and a plurality of analytical test strips (each with at least one extractor engagement feature) disposed in the cartridge housing. The test meter housing is configured for operative engagement with the cartridge housing and the test strip presentation mechanism is configured to present a single analytical test strip from the plurality of analytical test strips for engagement with the extractor. Moreover, the analytical test strip cartridge is configured for operative disposition in the desiccant vial.

21 Claims, 34 Drawing Sheets

U.S. PATENT DOCUMENTS

| | | |
|---|---|---|
| 2005/0281706 A1 | 12/2005 | Funke et al. |
| 2006/0266644 A1 | 11/2006 | Pugh et al. |
| 2006/0266765 A1* | 11/2006 | Pugh .................................. 222/1 |
| 2007/0084734 A1 | 4/2007 | Roberts et al. |
| 2007/0233395 A1* | 10/2007 | Neel et al. ....................... 702/19 |
| 2008/0167578 A1* | 7/2008 | Bryer et al. .................... 600/583 |
| 2009/0301899 A1 | 12/2009 | Hodges et al. |
| 2010/0025270 A1 | 2/2010 | Surridge et al. |
| 2010/0087754 A1* | 4/2010 | Rush et al. .................... 600/583 |
| 2011/0040165 A1 | 2/2011 | Williams, III |

\* cited by examiner

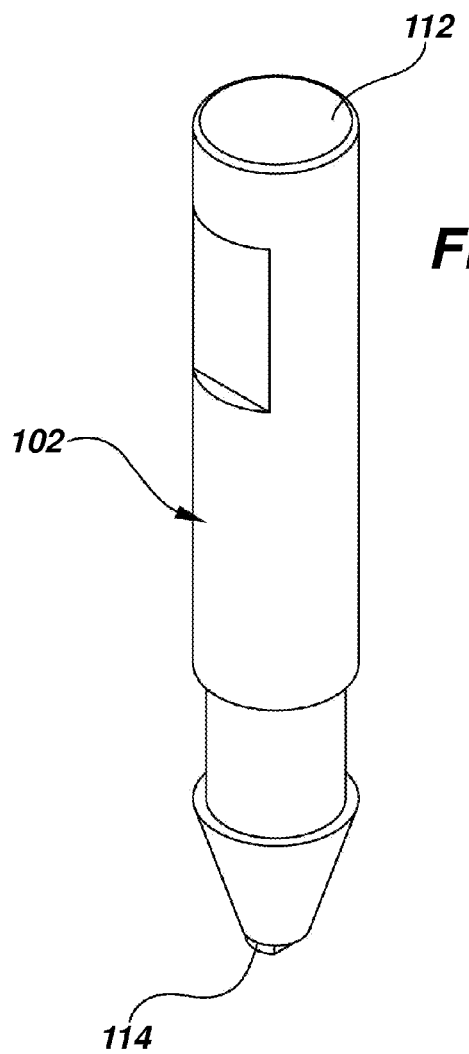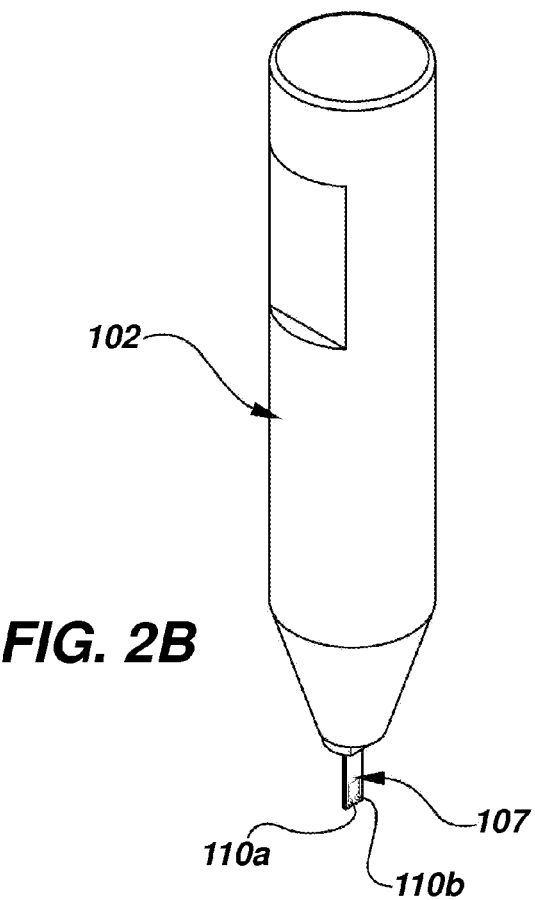
FIG. 2A
FIG. 2B

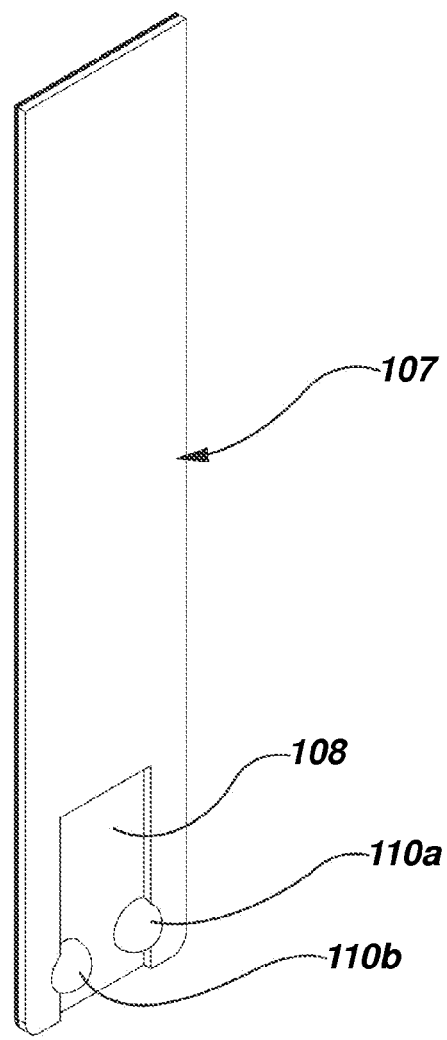
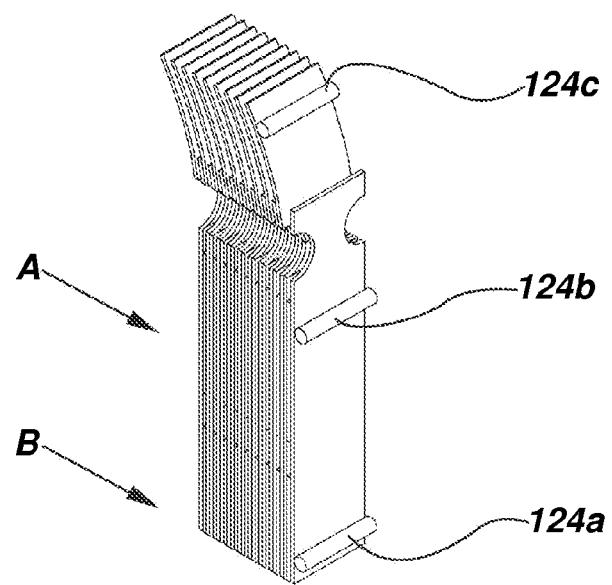
FIG. 8B

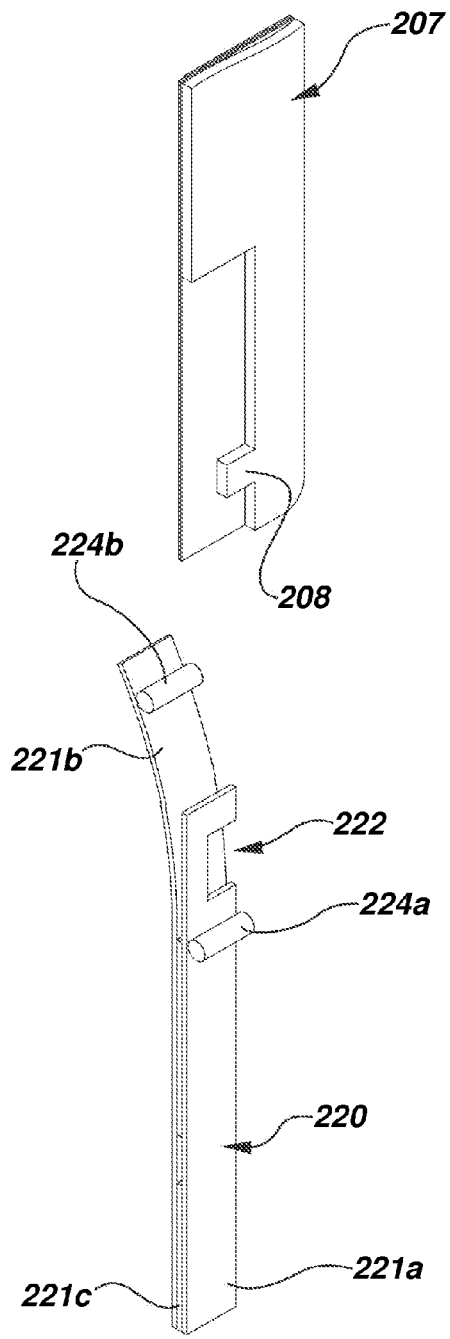
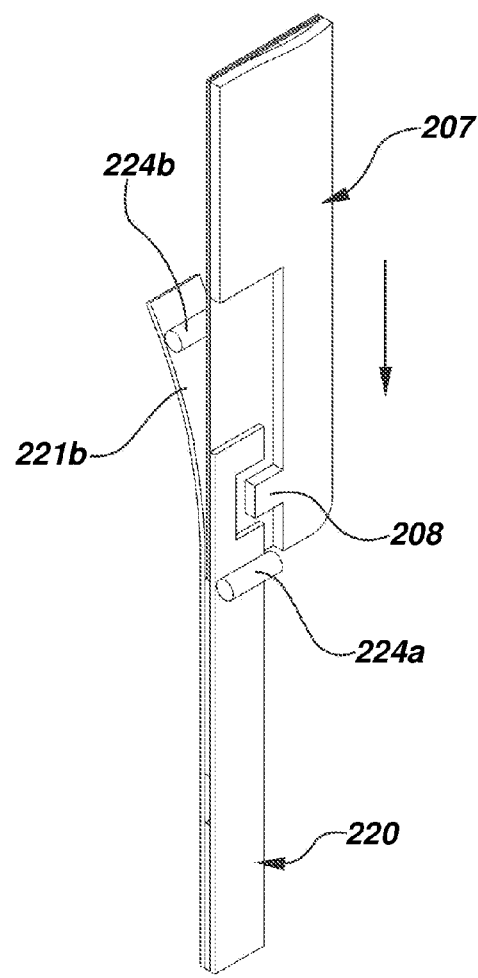
FIG. 12A
FIG. 12B

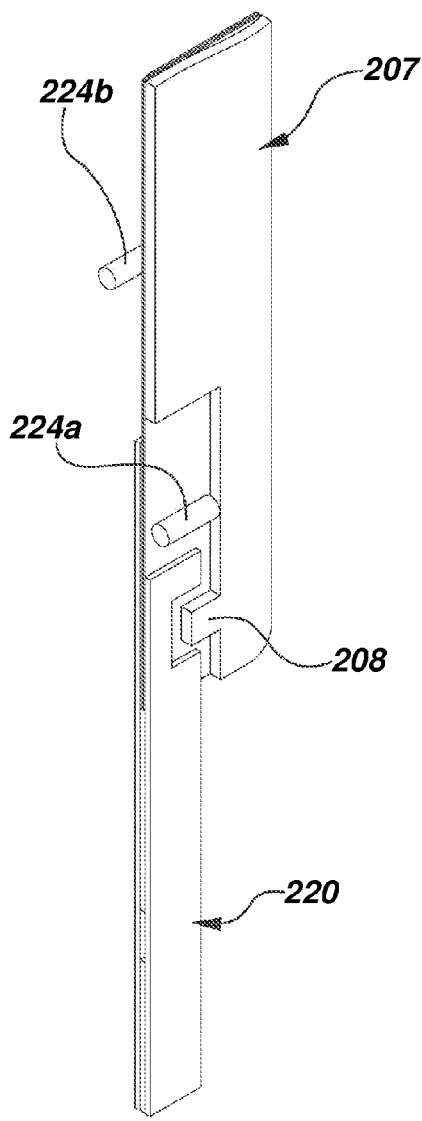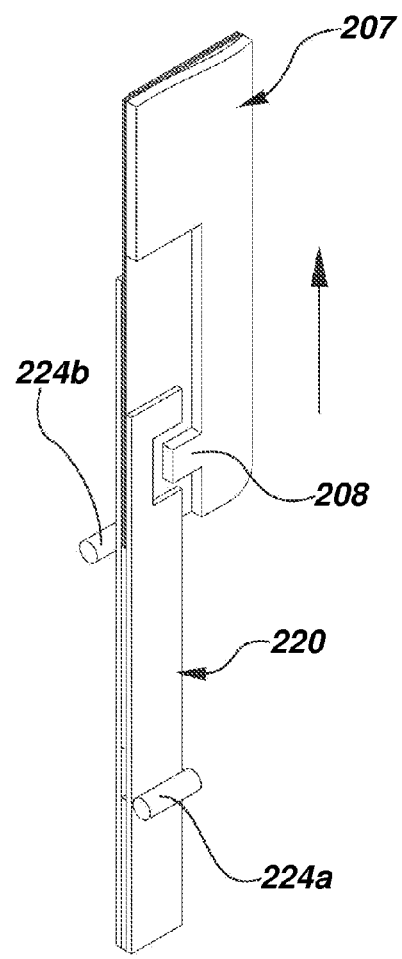
FIG. 12C
FIG. 12D

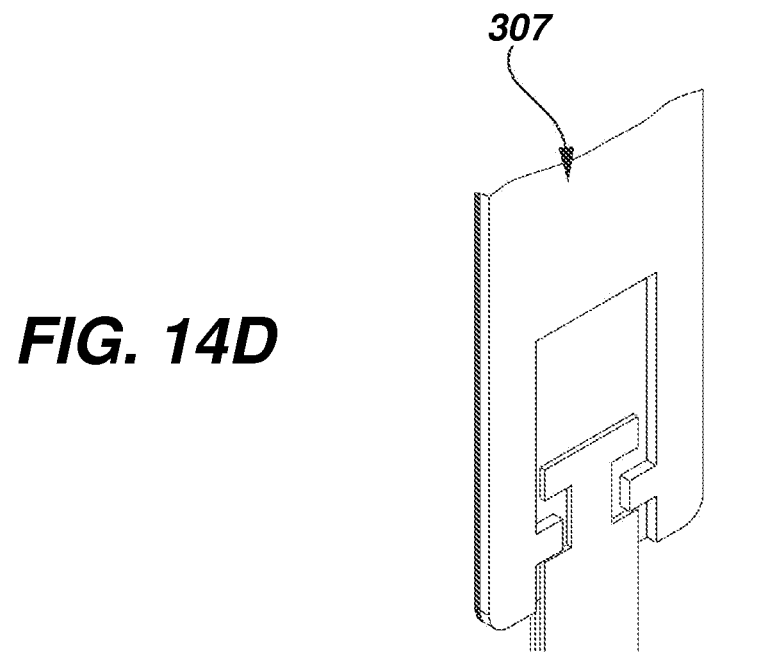
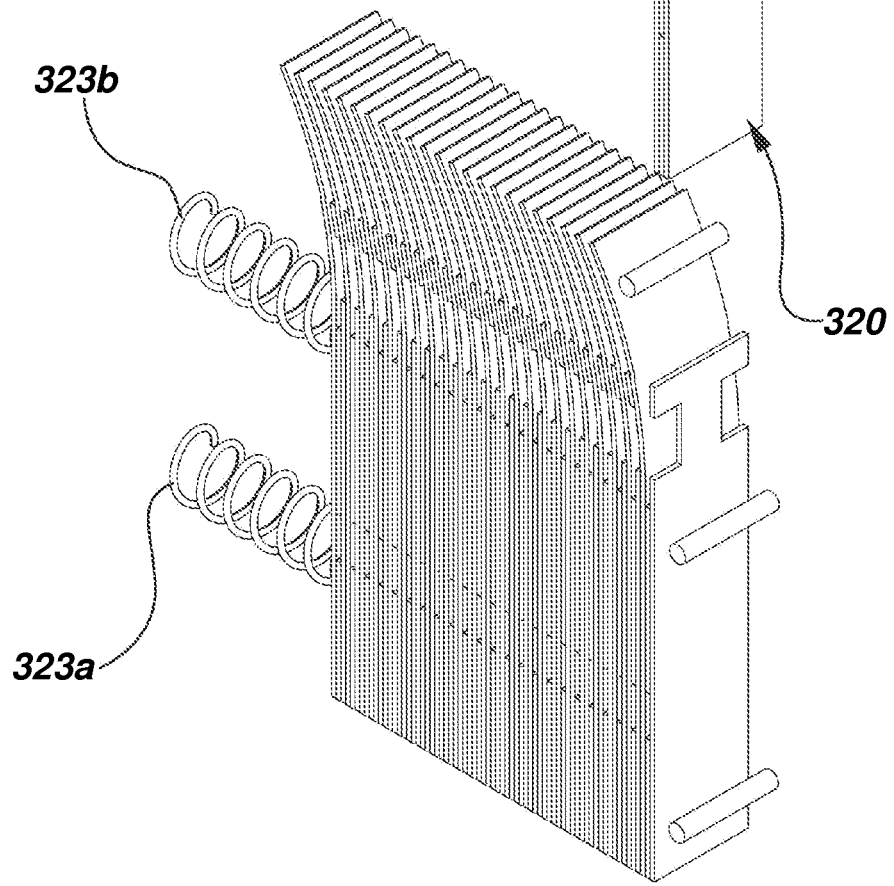
FIG. 14D

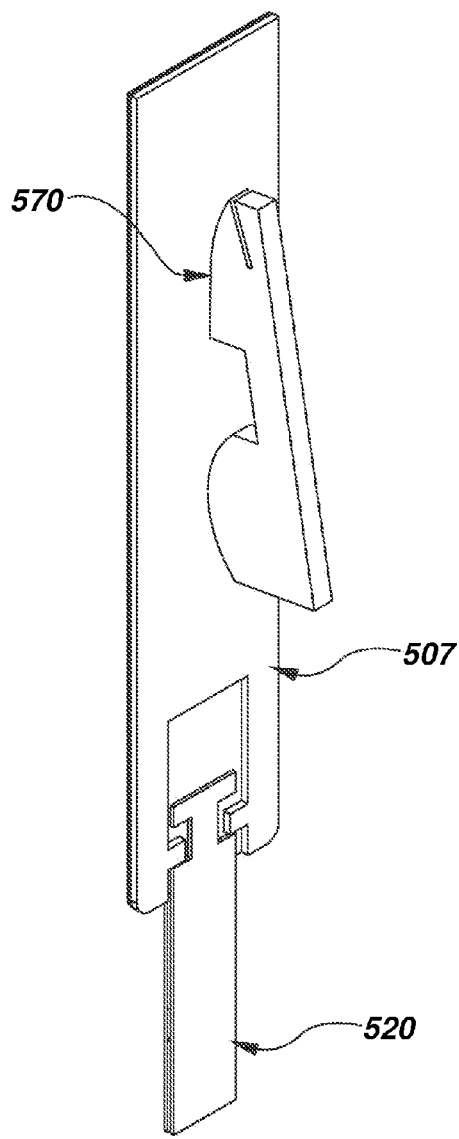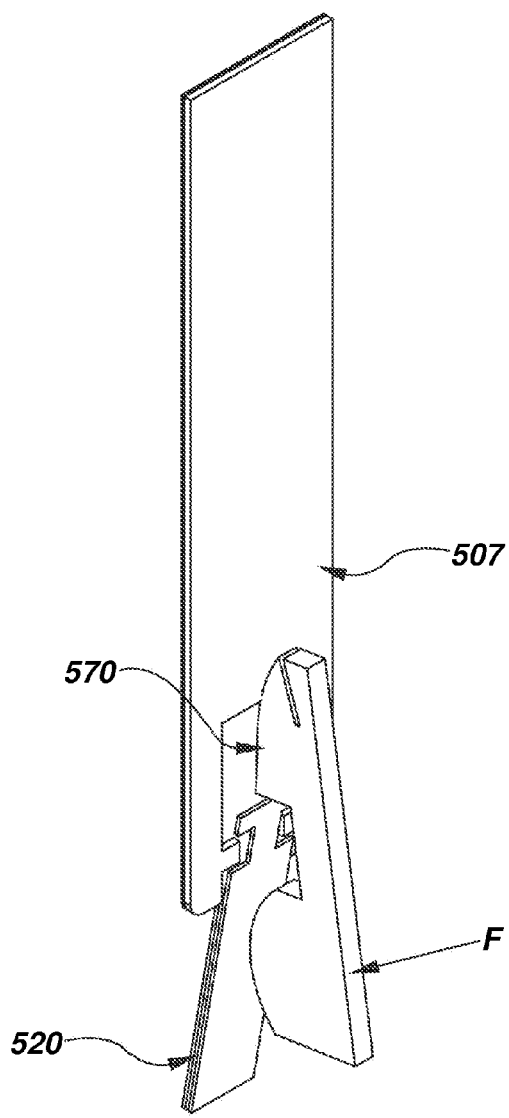
FIG. 18A
FIG. 18B

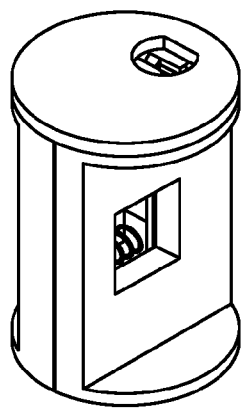
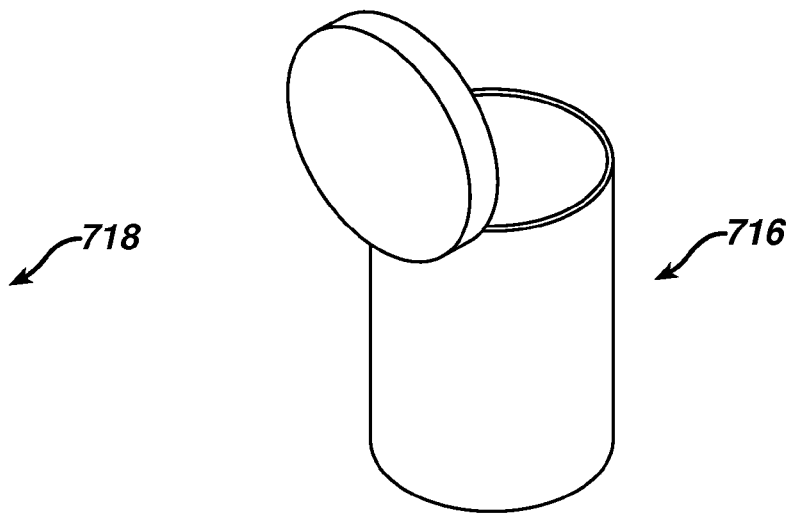
FIG. 23  FIG. 24
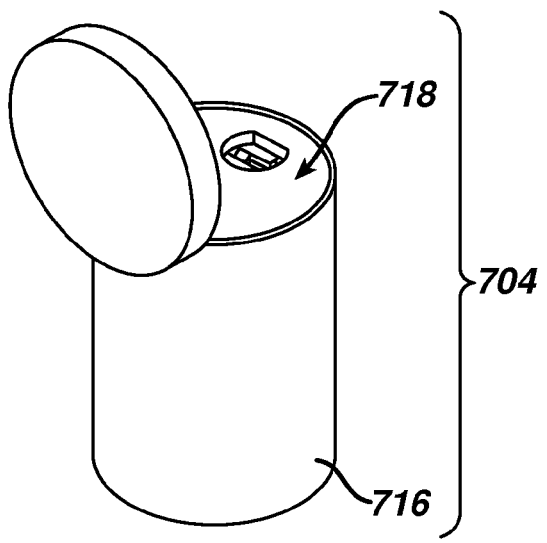
FIG. 25

HAND-HELD TEST METER AND ANALYTICAL TEST STRIP CARTRIDGE ASSEMBLY WITH DESICCANT VIAL

CROSS-REFERENCE

This application is a continuation-in-part application of U.S. application Ser. No. 13/198,536, filed Aug. 4, 2011, which is incorporated herein by reference in its entirety and to which application we claim priority under 35 USC §120.

BACKGROUND OF THE INVENTION

1. Field of the Invention

The present invention relates, in general, to medical devices and, in particular, to hand-held test meters and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

FIGS. 2A and 2B are simplified perspective depictions of the hand-held test meter of FIG. 1 with FIG. 2B illustrating an extractor of the hand-held test meter extending from a distal end of the hand-held test meter;

FIG. 8B is a simplified depiction of the extractor within the hand-held test meter of FIG. 8A and a plurality of analytical test strips and a portion of the test strip presentation mechanism within the analytical test strip cartridge of FIG. 8A;

FIGS. 12A, 12B, 12C and 12D are a sequence of simplified perspective depictions illustrating an alternative extractor and analytical test strip as can be employed in embodiments of the present invention in use;

FIGS. 14A, 14B, 14C and 14D are a sequence simplified perspective depictions illustrating another extractor (with a semicircular section of the extractor removed in FIGS. 14B and 14C to reveal components behind the extractor), as can be employed in embodiments of the present invention, and the analytical test strip of FIGS. 13A-B in use;

FIGS. 18A, 18B and 18C are a sequence of the simplified perspective drawings illustrating the operative of an extractor, analytical test strip and analytical test strip release mechanism according to an embodiment of the present invention;

FIG. 23 is a perspective view of the loaded analytical test strip cartridge of FIG. 22 in a closed state;

FIG. 24 is a simplified perspective view of the desiccant vial included in the analytical test strip cartridge assembly of FIG. 20;

FIG. 25 is a simplified perspective view of the analytical test strip cartridge assembly of FIG. 20.

DETAILED DESCRIPTION OF ILLUSTRATIVE EMBODIMENTS

Figure 1:
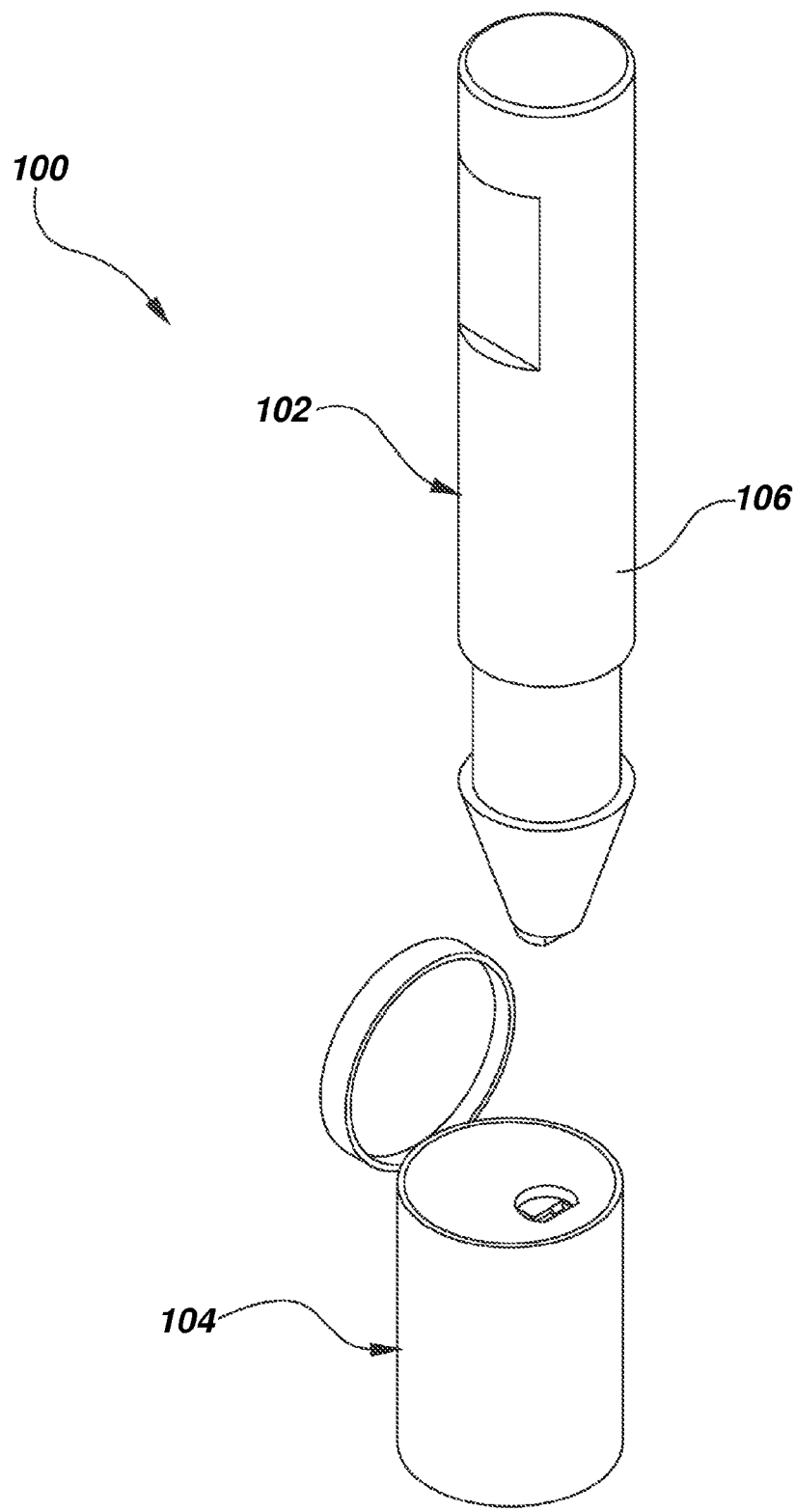
FIG. 1 is a simplified perspective depiction of a hand-held test meter and analytical test strip cartridge combination according to an embodiment of the present invention.
Figure 3A:
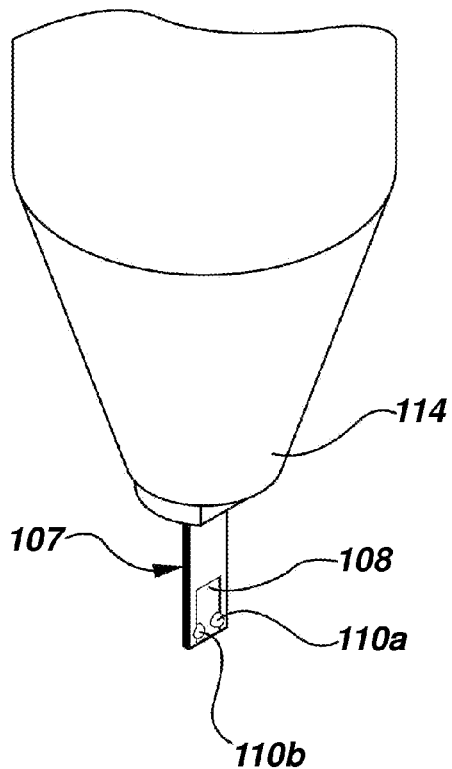
FIGS. 3A and 3B are simplified perspective depictions, front-angle and rear-angle respectively, illustrating the extractor and a portion of the hand-held test meter of FIG. 2B.
Figure 3B:
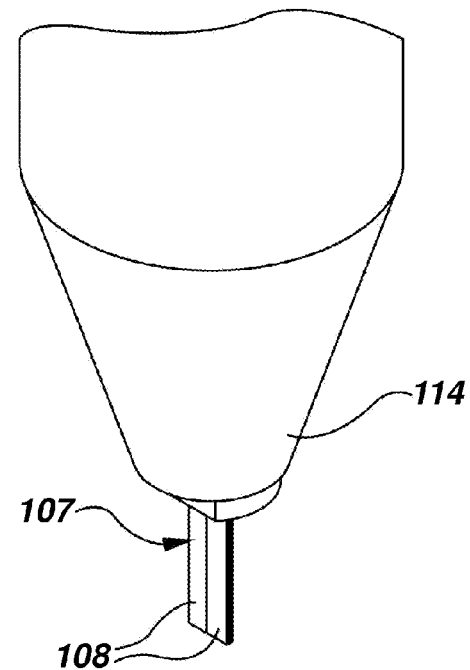
Figure 4A:
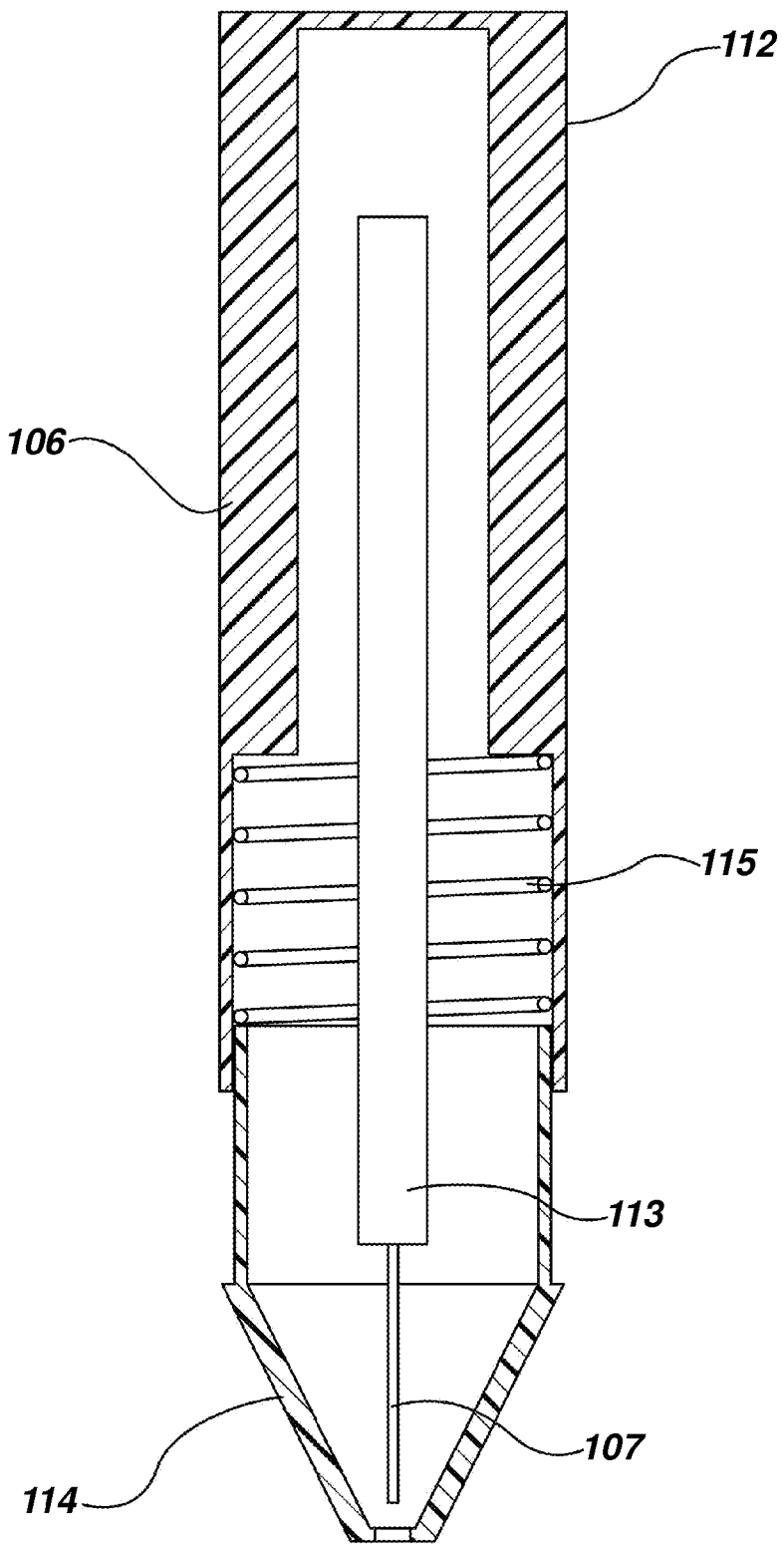
FIGS. 4A and 4B are simplified cross-sectional depictions of the hand-held test meter of FIG. 1 with FIG. 4B illustrating an extractor of the hand-held test meter extending from a distal end of the hand-held test meter.
Figure 4B:
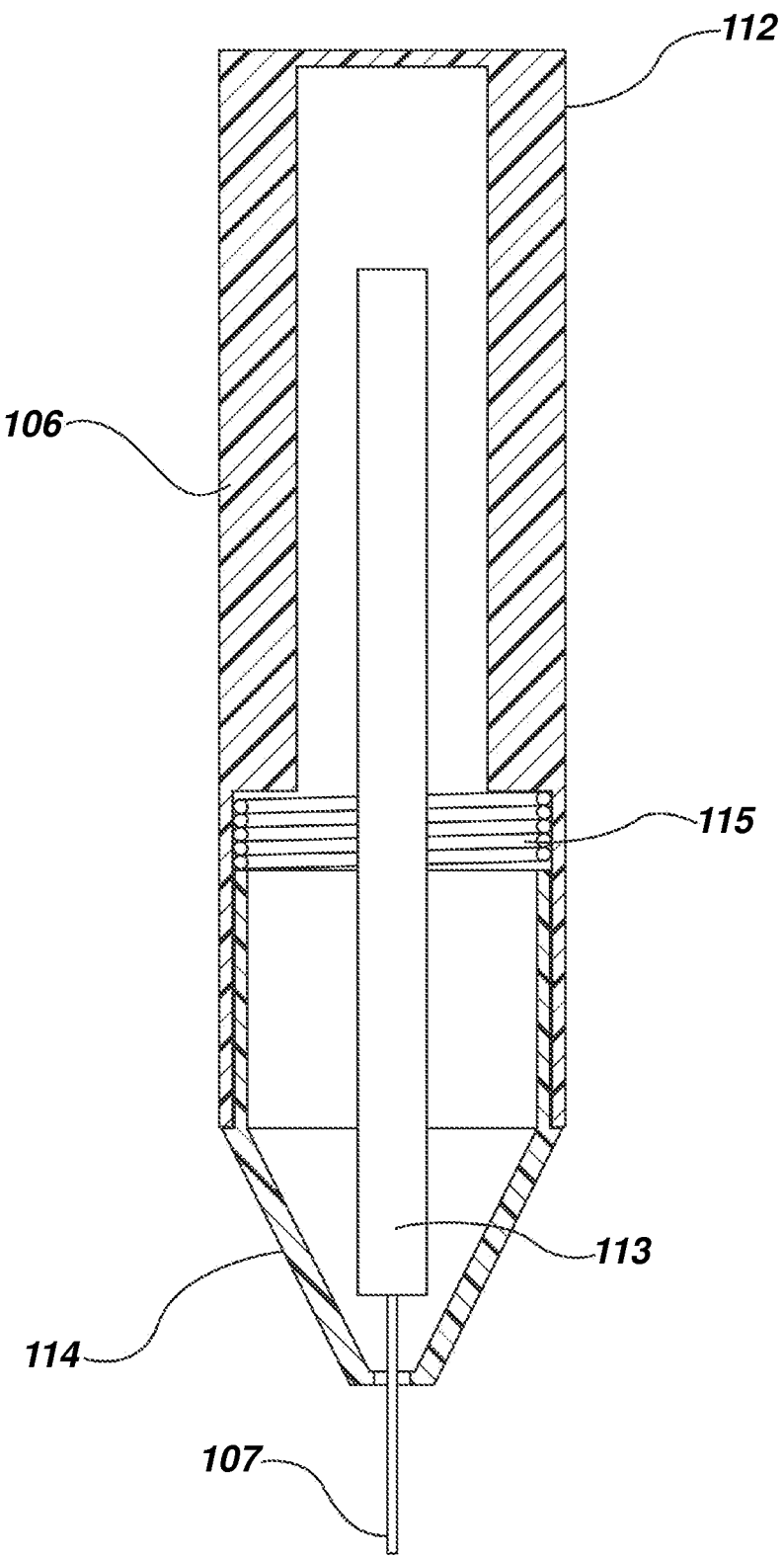

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, hand-held test meter and analytical test strip cartridge combinations according to embodiments of the present invention include a hand-held test meter and an associated analytical test strip cartridge. The hand-held test meter has a test meter housing and an extractor with at least one test strip engagement feature (such as a detent). The analytical test strip cartridge includes a cartridge housing, a test strip presentation mechanism disposed within the cartridge housing, and a plurality of analytical test strips (for example, an electrochemical-based analytical test strip and each with at least one extractor engagement feature) disposed in the cartridge housing.

In addition, the test meter housing is configured for operative engagement with the cartridge housing and the test strip presentation mechanism is configured to present a single analytical test strip from the plurality of analytical test strips for engagement with the extractor. Furthermore, the extractor and test meter housing are configured such that the extractor is operatively extendable from the test meter housing into the cartridge housing following engagement of the meter housing with the cartridge housing. The extractor is also configured such that, upon operative extension, the extractor mechanically engages with the analytical test strip presented by the test strip presentation mechanism via engagement between the at least one test strip engagement feature and the at least one extractor engagement feature, and such that, upon disengagement of the test meter housing from the cartridge housing, the extractor removes (i.e., extracts) the mechanically engaged analytical test strip from the cartridge housing and retracts into the test meter.

Such a hand-held test meter and analytical test strip cartridge "combination" can be considered hand-held test meter and analytical test strip cartridge "set" or hand-held test meter and analytical test strip cartridge "pairing."

Hand-held test meter and analytical test strip cartridge combinations according to embodiments of the present invention are particularly beneficial in that an analytical test strip is extracted from the analytical test strip cartridge and mechanically and, in some embodiments, electrically engaged with the hand-held test meter without any direct handling of the analytical test strip by a user. Since conventional analytical test strips are often relatively small, a user may have difficulty removing them from a cartridge and inserting them into a hand-held test meter. However, hand-held test meter and analytical test strip combinations according to embodiments of the present invention do not require a user to directly handle the analytical test strip. In addition, hand-held test meter and analytical test strip cartridge combinations according to embodiments of the present invention do not require expensive high tolerance mechanisms to push a single analytical test strip (which is relatively thin and, therefore, difficult to accurately push) from the analytical test strip cartridge since the extractor extends into the analytical test strip cartridge and mechanically engages the analytical test strip.

Referring to FIGS. 1 through 11, hand-held test meter and analytical test strip cartridge combination 100 includes a hand-held test meter 102 and an analytical test strip cartridge 104.

Hand-held test meter 102 includes a test meter housing 106 and an extractor 107 with three extractor electrical contacts 108 and test strip engagement features 110a and 110b. Hand-held test meter 102 also has a proximal end 112, a printer circuit board 113, a distal end 114 and a spring 115.

Once apprised of the present disclosure, one skilled in the art will recognize that hand-held test meter 102 and/or printed circuit board 113 thereof includes suitable components for the determination of an analyte in a bodily sample applied to an analytical test strip engaged with extractor 107. For the sake of simplicity and clarity, such suitable components are not depicted in the figures nor fully described herein. However, conventional hand-held test meters for the determination of an analyte in a bodily fluid sample are described in, for example, U.S. Pat. No. 7,468,125 and U.S. Patent Application Publication No.s 2009/0301899 and 2007/0084734, each of which is hereby incorporated in full by reference.

Analytical test strip cartridge 104 includes a cartridge housing 116, a test strip presentation mechanism 118 disposed in the cartridge housing and a plurality of analytical test strips 120 disposed in the cartridge housing in a stacked configuration (see FIGS. 5A, 5B, 5C and 7 in particular).

Figure 6:
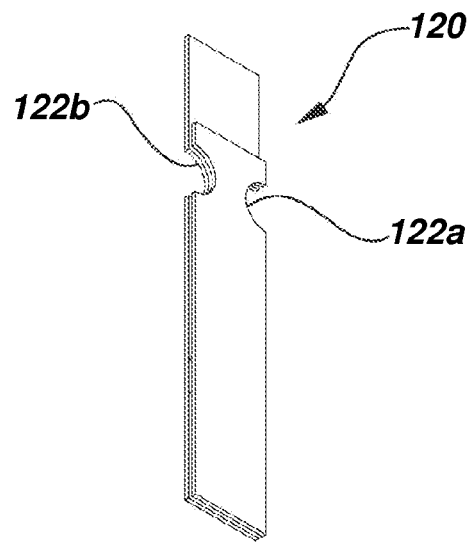
FIG. 6 is a simplified perspective depiction of a single analytical test strip which can be employed in embodiments of the present invention including in the stacked configuration of FIGS. 5A-5C.
Figure 7:
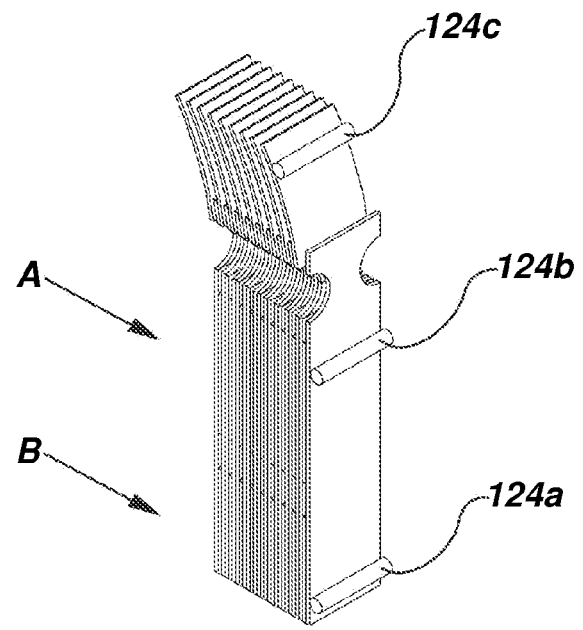
FIG. 7 is a simplified perspective depiction of the plurality of analytical test strips disposed in a stacked configuration and a portion of the test strip presentation mechanism of FIGS. 5A-5C.

Each of the plurality of analytical test strips includes two extractor engagement features 122a and 122b (see FIG. 6 in particular). Extractor engagement features 122a and 122b are essentially semicircular notches configured to engage with test strip engagement features 110a and 110b in a detent-like manner. One skilled in the art will recognize that test strip engagement features 110a and 110b are spherical protrusions that serve as "detents" in that they position and hold the extractor and analytical test strip in relationship to one another in a releasable manner such that the analytical test strip can be released by applying a force thereto. The releasing of an analytical test strip mechanically engaged with an extractor will be described in more detail with respect to FIGS. 18A through 18C below.

Although, for the purpose of illustration only, extractor engagement features test strip engagement features are depicted in this Specification as notices and detents, or notches and tabs, any suitably shaped protrusions, indentations and other designs can be employed so long as they can cooperate with each other.

Figure 5A:
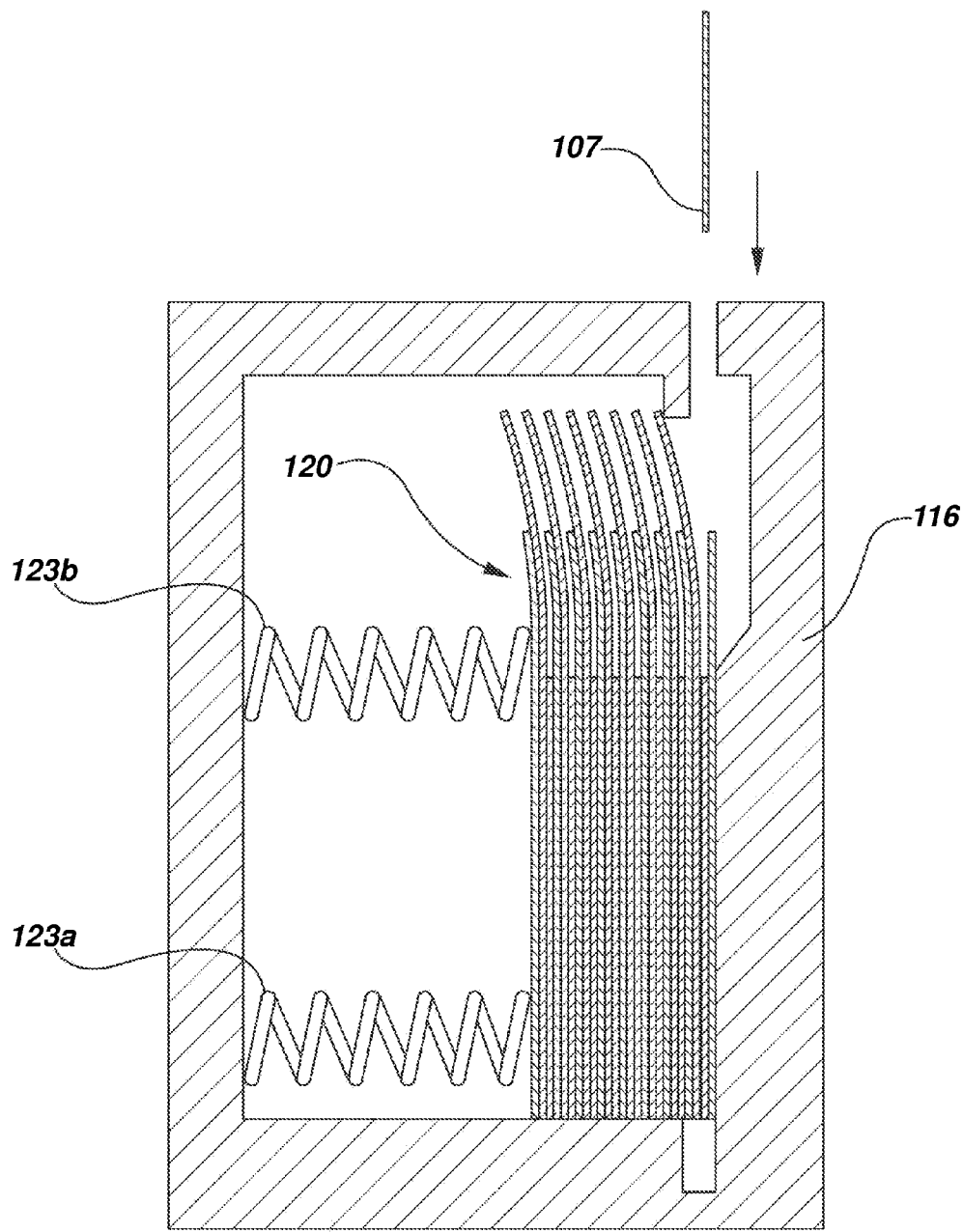
FIGS. 5A, 5B and 5C are a sequence of simplified cross-sectional depictions of the analytical test strip cartridge of FIG. 1 (illustrating a cartridge housing, test strip presentation mechanism of the analytical test strip cartridge and also illustrating a plurality of analytical test strips disposed in the cartridge housing in a stacked configuration) depicting the extraction of a single analytical test strip therefrom by an extractor of the hand-held test meter of FIG. 1.
Figure 5B:
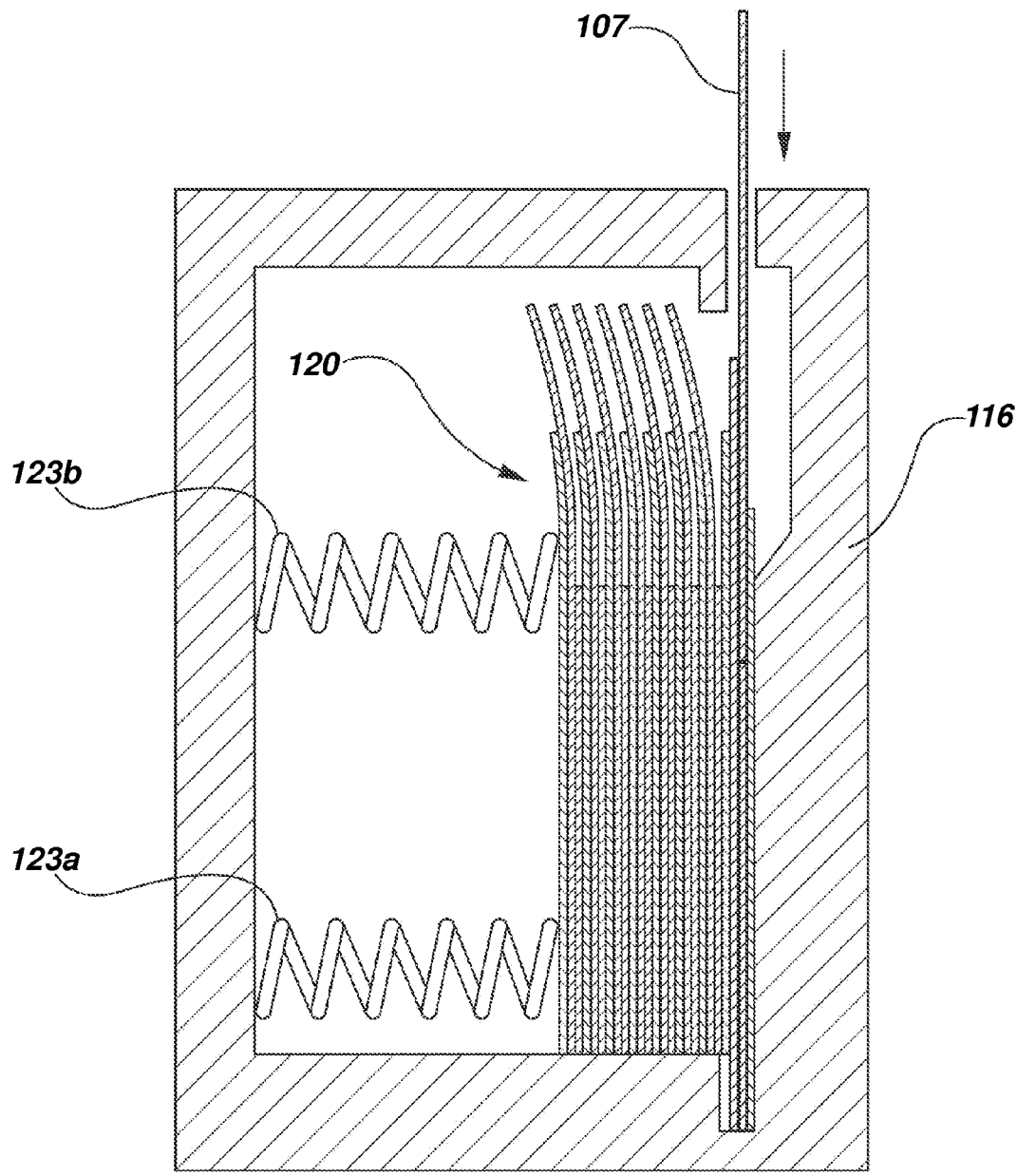
Figure 5C:
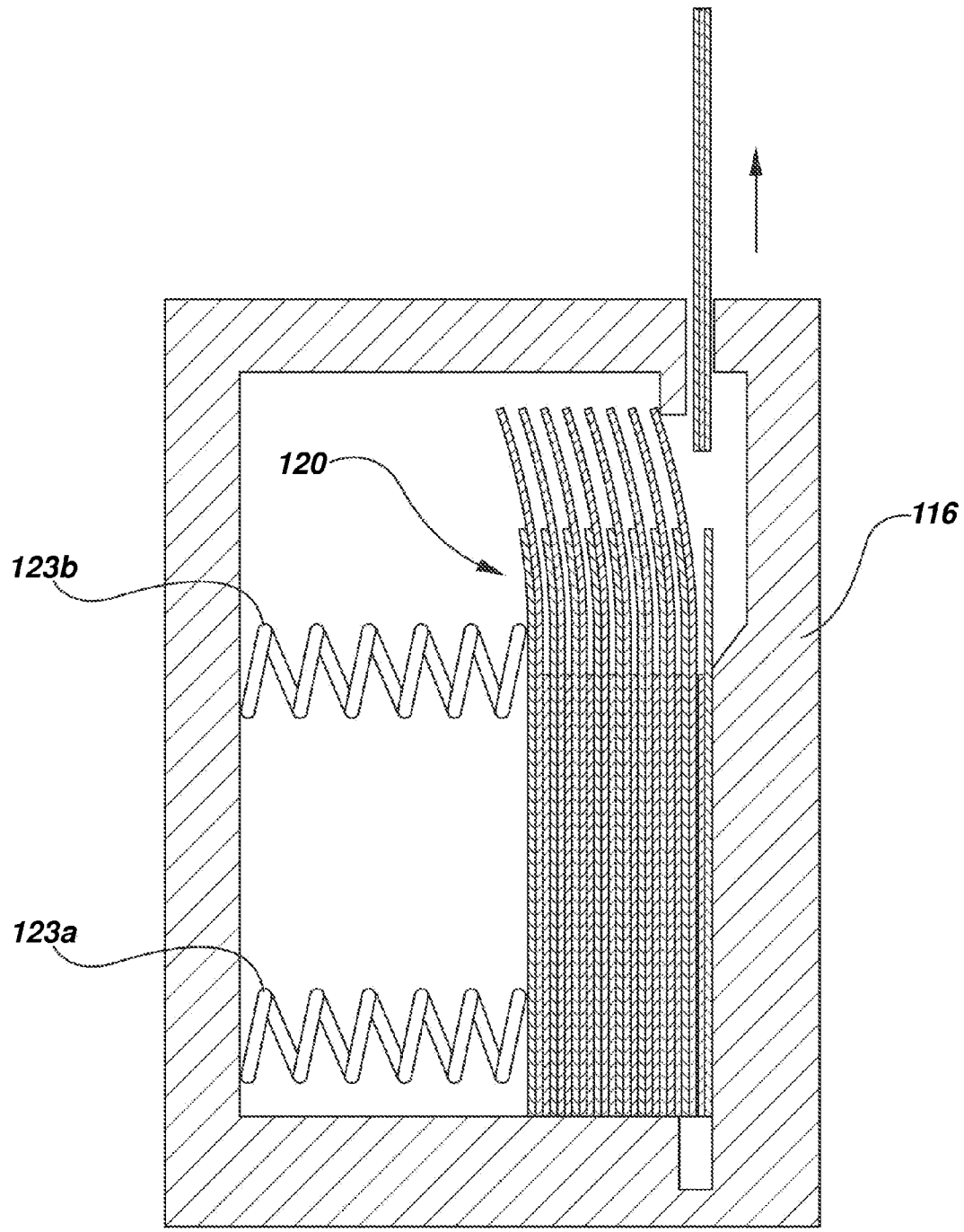

Test strip presentation mechanism 118 includes three test strip restraints 124a, 124b and 124c (depicted in FIGS. 7, 8B, 9B, 9C, 10B but omitted for clarity from FIGS. 5A-5C). Test strip presentation mechanism 118 also includes springs 123a and 123b (see FIGS. 5A through 5C).

Figure 8A:
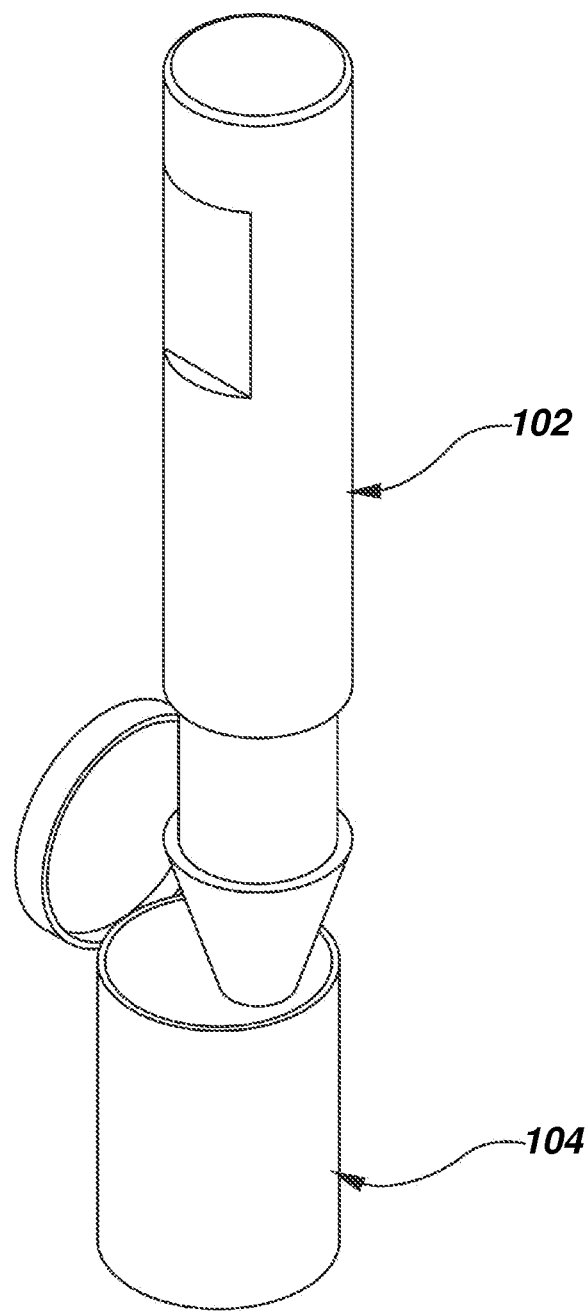
FIG. 8A is a simplified perspective depictions of the hand-held test meter of FIG. 1 engaged with the analytical test strip cartridge of FIG. 1.
Figure 9A:
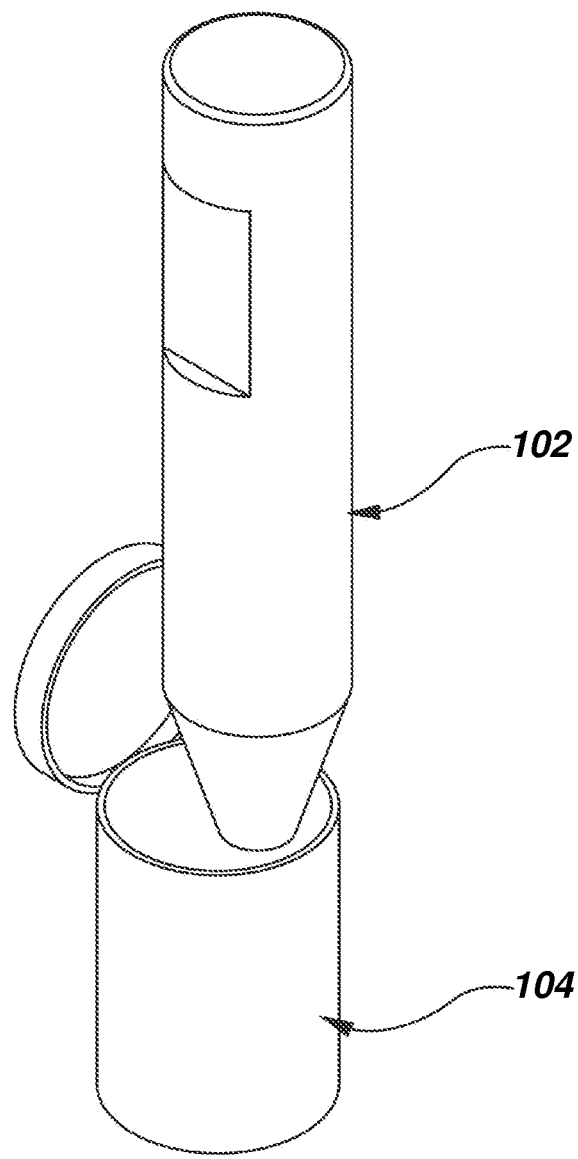
FIG. 9A is a simplified perspective depictions of the hand-held test meter of FIG. 1 engaged with the analytical test strip cartridge of FIG. 1 in a position such that the extractor is extended within the analytical test strip cartridge.
Figures 9B, 9C:
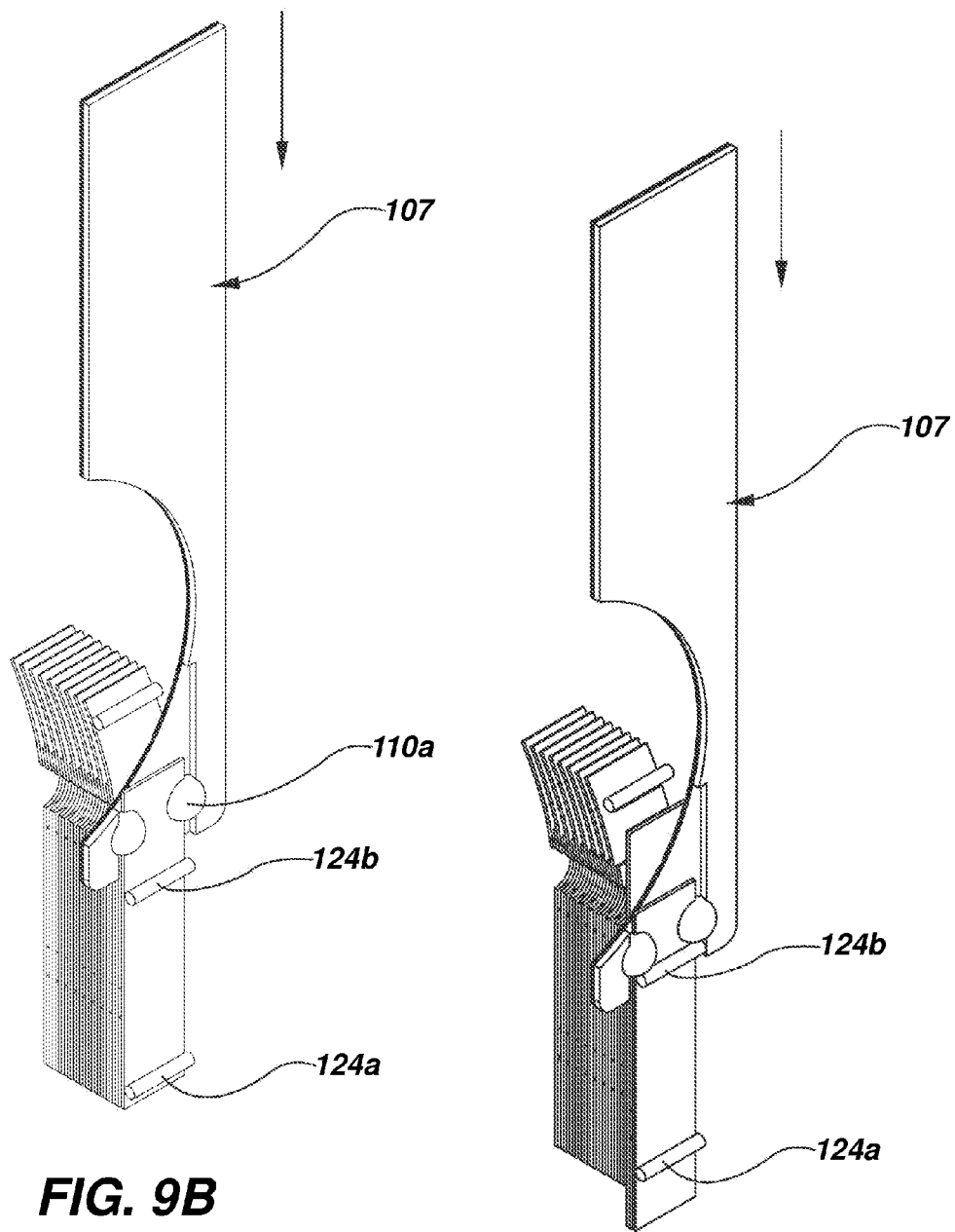
FIGS. 9B and 9C are simplified depictions of the extractor (with a semicircular section removed to reveal components behind the extractor), the plurality of analytical test strips and a portion of the test strip presentation mechanism within the analytical test strip cartridge of FIG. 9A that illustrates their interaction as the extractor is extended from the distal end of the hand-held test meter.

Springs 124a and 124b press against the stacked configuration of analytical test strips (see, for example, FIGS. 5A-5C, arrows A and B in FIGS. 7 and 8B and the similar configuration of FIGS. 14A through 14D), while test strip restraints 124a, 124b and 124c serve to splay apart top and bottom layers of analytical test strip 120 such that extractor 107 can mechanically engage the analytical test strip (see, for example, FIGS. 8B and 9B). Such top and bottom layers are further described below with respect to FIGS. 12A-12D and 13A and 13B.

In the embodiment of FIGS. 1 through 11, each of the analytical test strips 120 has three strip electrical contacts (not depicted in FIGS. 1-11) configured to make electrical contact with the three extractor electrical contacts. Such electrical contacts are electrically conductive layers on the surface of extractor 107 and the surface(s) of analytical test strip 120 and disposed such that an operable electrical connection is made therebetween when extractor 107 is engaged with analytical test strip 120.

Figure 10A:
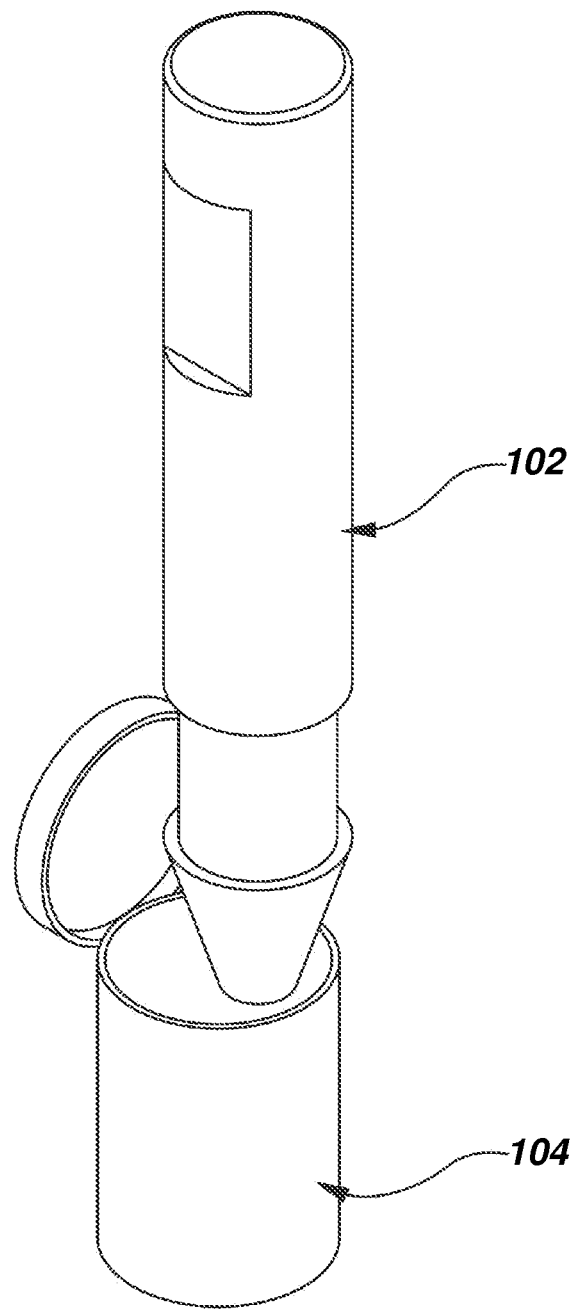
FIG. 10A is a simplified perspective depictions of the hand-held test meter of FIG. 1 engaged with the analytical test strip cartridge of FIG. 1 in a position such that the extractor is retracted within the analytical test strip cartridge.
Figure 10B:
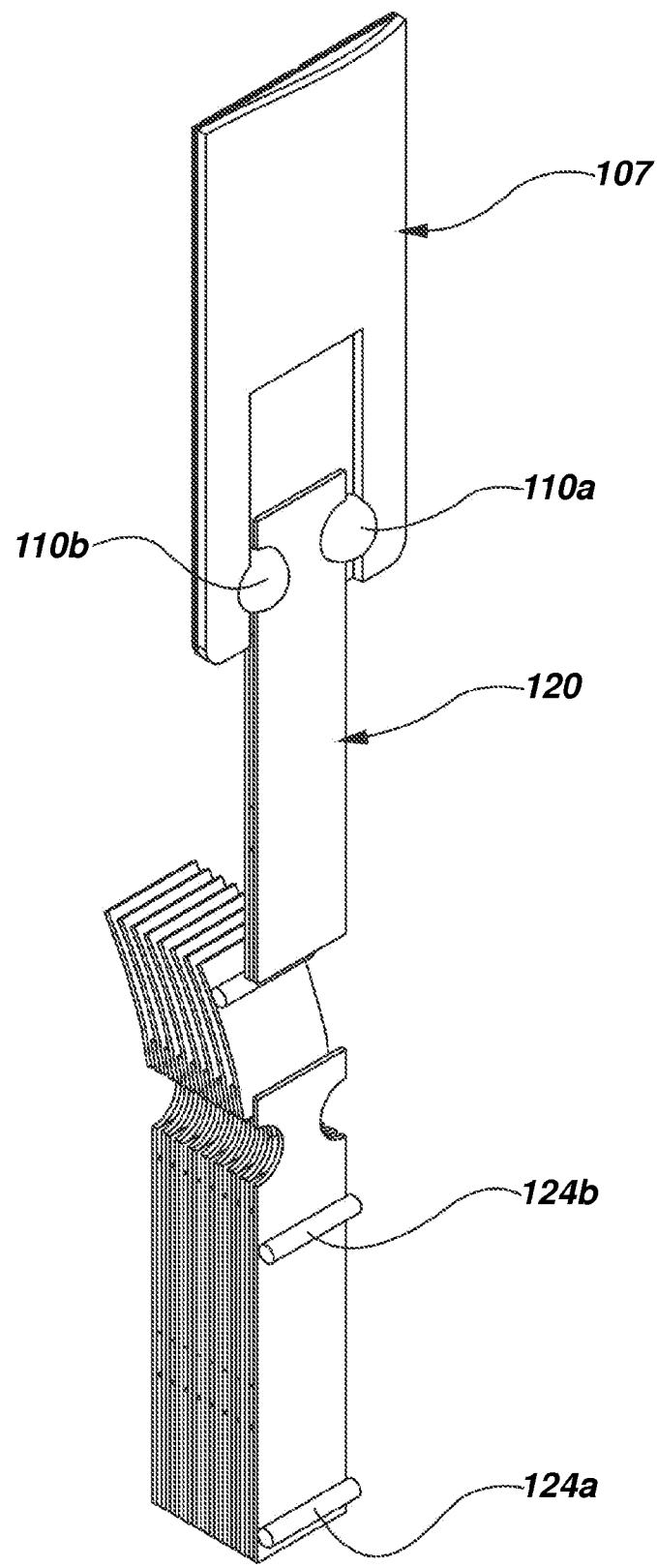
FIG. 10B is a simplified depiction of the extractor, a single analytical test strip mechanically engaged with the extractor, the remainder of the plurality of analytical test strips, and a portion of the test strip presentation mechanism within the hand-held test meter and analytical test strip cartridge combination as depicted in FIG. 10A.
Figure 11:
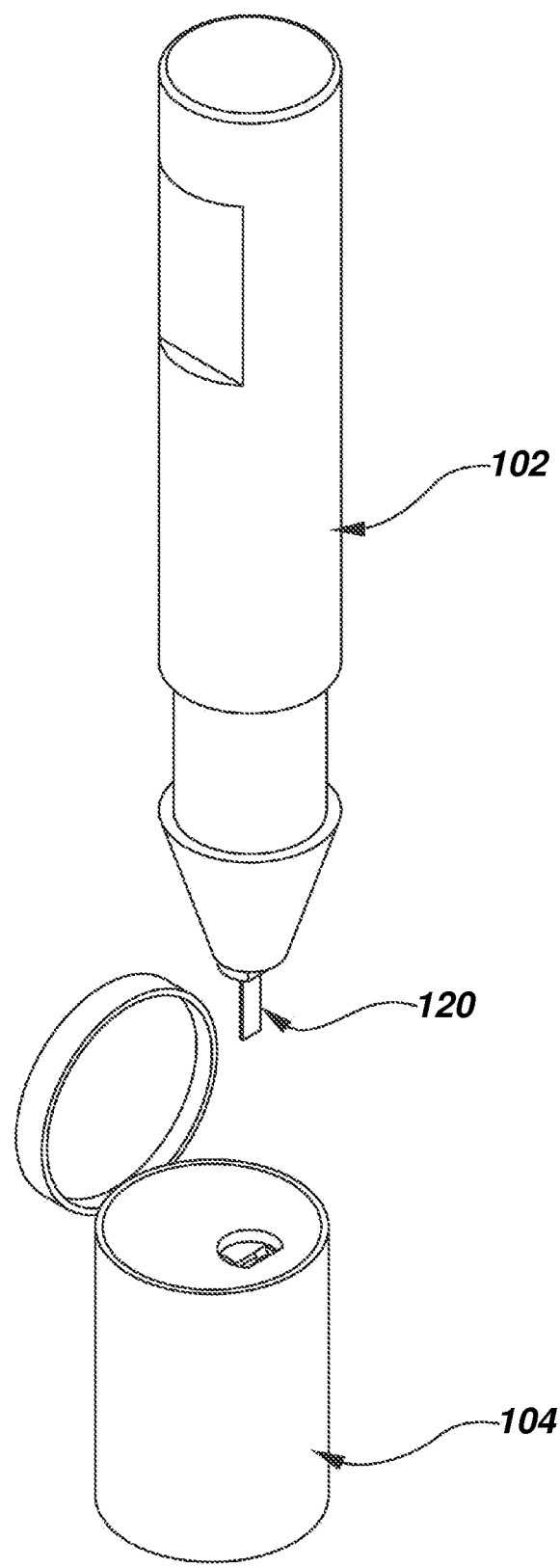
FIG. 11 is a simplified depiction of the hand-held test meter and analytical test strip cartridge of FIG. 1 with the hand-held test meter disengaged from the analytical test strip cartridge and an analytical test strip mechanically engaged with the extractor.

Test meter housing 106 is configured for operative engagement with analytical test strip cartridge 104 as depicted, for example, in FIGS. 8A, 9A and 10A. Such an operative engagement can be, for example, based on a "lock and key" configuration that serves to align extractor 107 with an analytical test strip presented by test strip presentation mechanism 118. FIGS. 8A and 8B illustrate such an engagement and alignment, respectively.

Test strip presentation mechanism 118 is configured to present a single analytical test strip from the plurality of analytical test strips for engagement with the extractor (see FIGS. 5A, 8B, 9B, and 9C in particular).

Extractor 107 and test meter housing 106 are configured such that extractor 107 is operatively extendable from test meter housing 106 into analytical test strip cartridge 104 upon engagement of test meter housing 106 with analytical test strip cartridge 104. In the embodiment of FIGS. 1 through 11, such extension of the extractor is achieved by manual compression of the distance between proximal end 112 and distal end 114 of hand-held test meter 102 against the force of spring 115 (compare, for example, FIGS. 2A and 2B, FIGS. 4A and 4B, and FIGS. 8A and 9A). In such compression, distal end 114 slides over a portion of test meter housing 106 such that extractor 107 extends from distal end 114 and into analytical test strip cartridge 104. This is accomplished by a user pushing downward on proximal end 112 while distal end 114 is held stationary by engagement with analytical test strip cartridge 104.

Extractor 107 is configured such that, upon operative extension into the cartridge housing, it mechanically engages with an analytical test strip 120 presented by the test strip presentation mechanism. Such mechanical engagement occurs between test strip engagement feature 110a and 110b of extractor 107 and the extractor engagement features 122a and 122b of the analytical test strip 120.

FIG. 9B depicts such a mechanical engagement as extractor 107 is extended into analytical test strip cartridge 104 and comes into operative contact with an analytical test strip 120 that has been presented for engagement. Further extension of extractor 107 serves to push analytical test strip 120 downward and, thereby, release analytical test strip 120 from retainer 124c (see, for example, FIGS. 5B and 9C).

Extractor 107 is also configured such that, upon disengagement of the test meter housing from the analytical test strip cartridge, it removes the mechanically engaged analytical test strip from the cartridge housing and retracts into the test meter housing with the extracted analytical test strip exposed for application of a bodily fluid sample (see FIG. 11) and the determination of an analyte in the bodily fluid sample by the hand-held test meter.

Once apprised of the present disclosure, one skilled in the art will recognize that hand-held test meter 102 will include such electronics and other components that are required or desired for the determination of an analyte (such as glucose) in a whole blood sample (such as a whole blood sample) applied to analytical test strip 120 after analytical test strip 120 has been extracted from analytical test strip cartridge 104. However, such electronics and other components (other than printed circuit board 113) are not depicted in the figures to avoid obscuring the beneficial features and functions of the present invention.

Hand-held test meter and analytical test strip cartridge combinations according to embodiments of the present invention can be formed of any suitable materials known to one skilled in the art and manufactured using any suitable techniques.

FIGS. 12A, 12B, 12C and 12D are a sequence of simplified perspective depictions illustrating an alternative extractor 207 and analytical test strip 220 as can be employed in embodiments of the present invention. Extractor 207 includes a single test strip engagement feature 208 in the form of a tab. Analytical test strip 220 includes a top layer 221a, a bottom layer 221b and a spacer layer 221c. Analytical test strip 220 also includes an extractor engagement feature 222 in the form of a notch in top layer 221a.

Once apprised on the present disclosure, one skilled in the art will recognize that analytical test strips employed in embodiments of the present invention will include suitable layers, reagents (e.g., enzymatic reagents) and features (such as working, reference and counter electrodes) in addition to those depicted and described herein. For the sake of simplicity and clarity, such suitable layers, reagents and features are not depicted in the figures nor fully described herein. However, conventional analytical test strips for the determination of an analyte in a bodily fluid sample are described in, for example, U.S. Pat. Nos. 5,708,247; 5,951,836; 6,241,862; and 6,284,125; each of which is hereby incorporated in full by reference.

FIG. 12A depicts analytical test strip 220 being presented with top layer 221a splayed apart from bottom layer 221b by test strip retainers 224a and 224b of a test strip presentation mechanism. As extractor 207 is extended from the distal end of a hand-held test meter (not shown) in the direction of the arrow in FIG. 12B, it slips between top layer 221a and bottom layer 221b and test strip engagement feature 208 mechanically engages with extractor engagement feature 222 (see FIG. 12B).

As extractor 207 extends further, it pushes analytical test strip 220 free of test strip retainer 224b (see FIG. 12C). When the hand held-test meter (not shown) of which extractor 207 is a component is disengaged from the analytical test strip cartridge (also not shown) containing analytical test strip 120 and test strip retainers 224a and 224b, extractor 207 removes (i.e., extracts) analytical test strip 220 in the direction of the arrow in FIG. 12D.

Figure 13A:
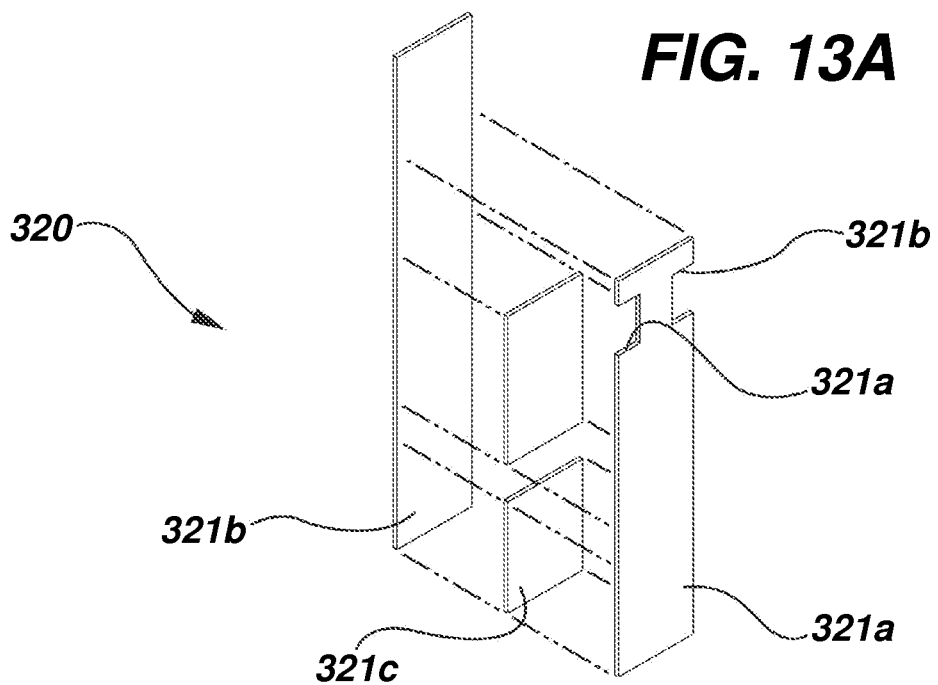
FIGS. 13A and 13B are simplified exploded and simplified perspective depictions, respectively, of an analytical test strip as can be employed in embodiments of the present invention.
Figure 13B:
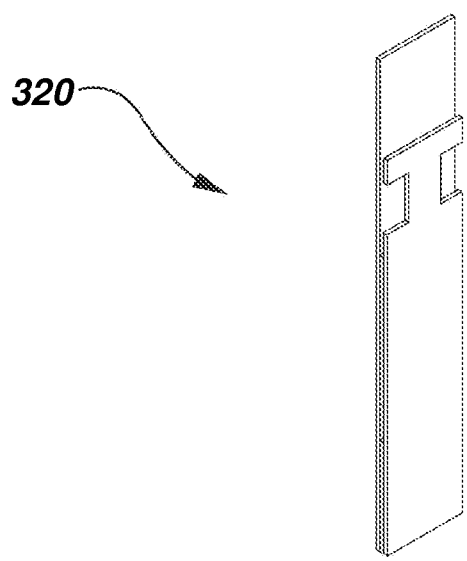

FIGS. 13A and 13B are simplified exploded and simplified perspective depictions, respectively, of an analytical test strip 320 as can be employed in embodiments of the present invention. FIGS. 14A, 14B, 14C and 14D are a sequence simplified perspective depictions illustrating another extractor 307, as can be employed in embodiments of the present invention, and analytical test strip 320 in use. FIGS. 15A and 15B are simplified perspective depictions, front-angle and rear-angle respectively, illustrating extractor 307 and analytical test strip 320 following mechanical engagement of extractor 307 and analytical test strip 320.

Referring to FIG. 13A in particular, analytical test strip 320 includes a top layer 321a, a bottom layer 321b and a spacer layer 321c. Analytical test strip 320 also includes extractor engagement features 322a and 322b in the form of notches in top layer 321a.

Figure 14A:
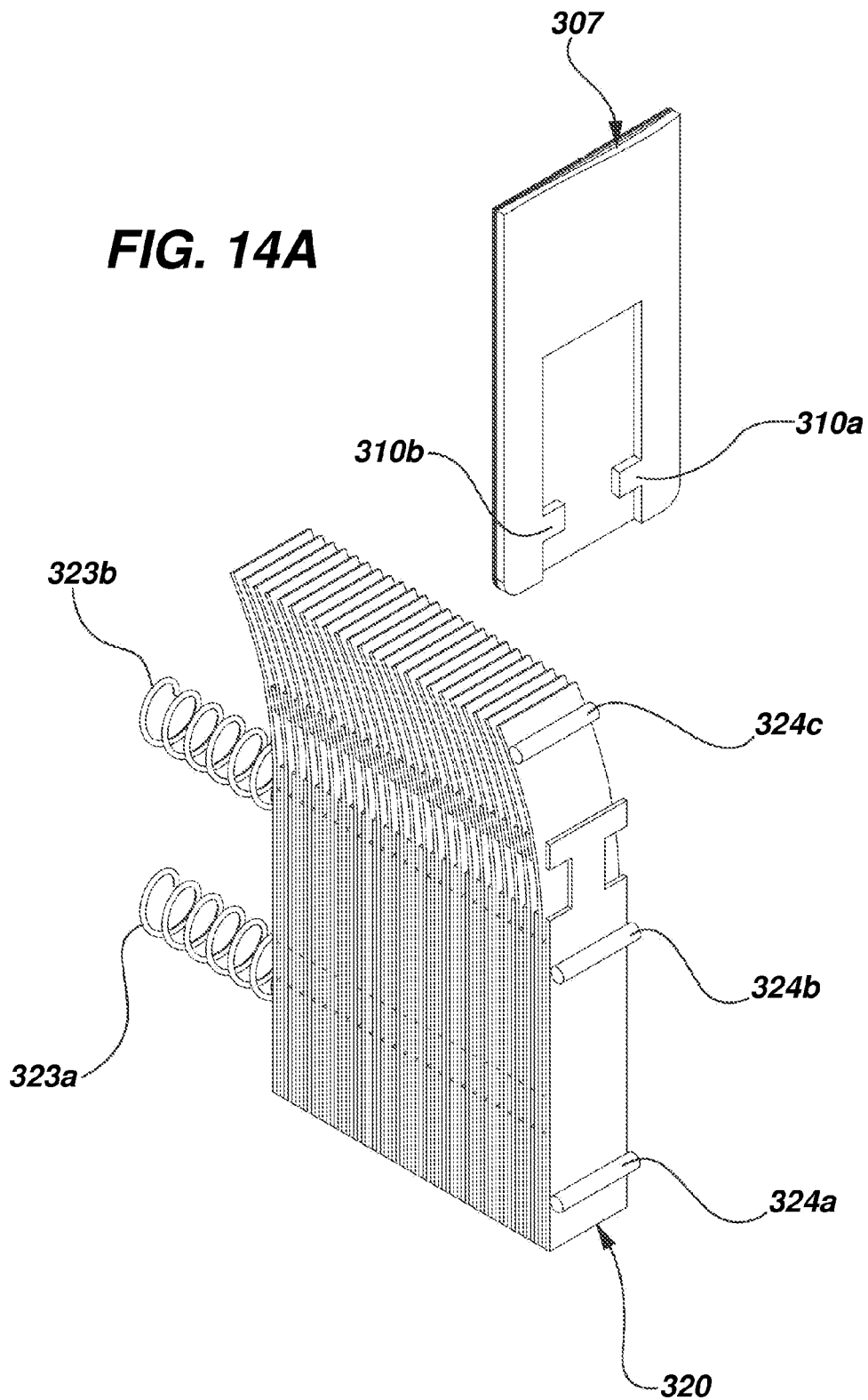
Figure 14B:
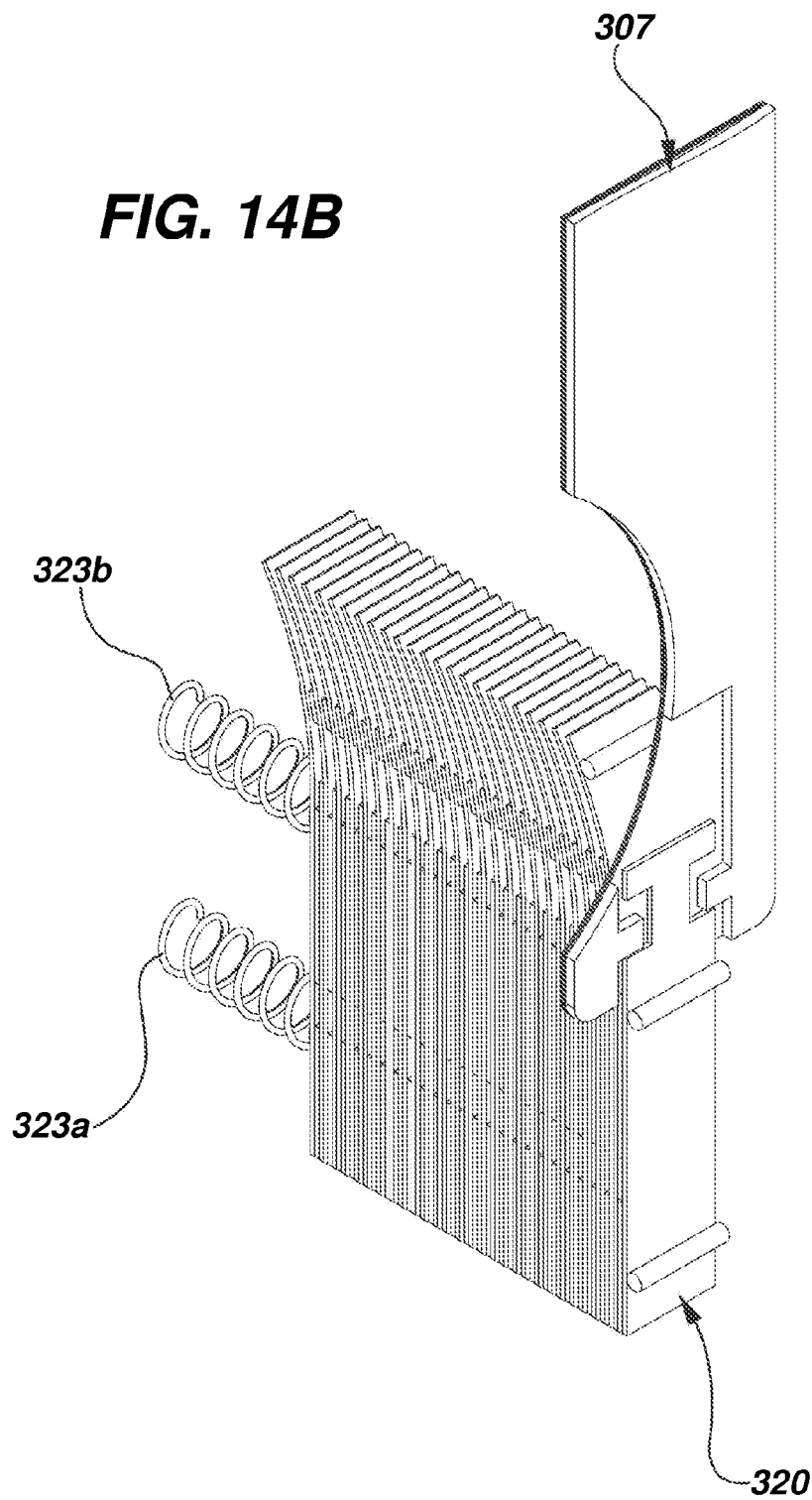
Figure 15A:
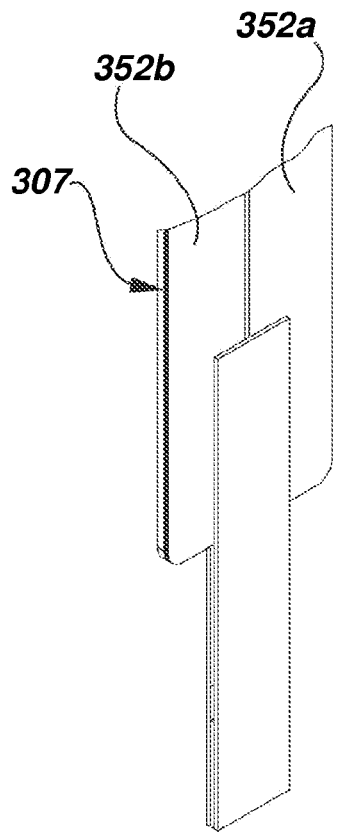
FIGS. 15A and 15B are simplified perspective depictions, front-angle and rear-angle respectively, illustrating the extractor and analytical test strip of FIG. 14D.
Figure 15B:
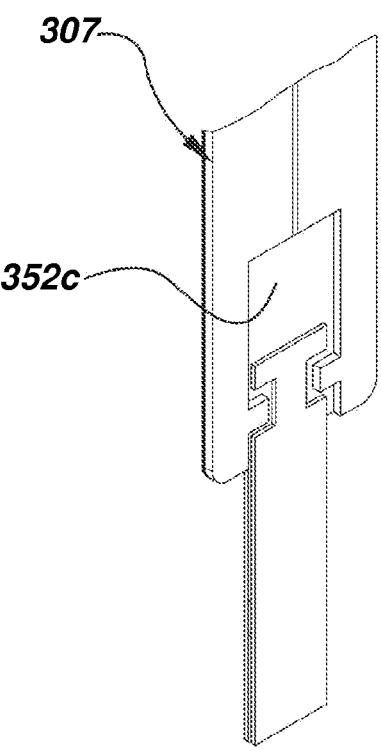

As depicted in, for example, FIG. 14A, a test strip presentation mechanism (i.e., springs 323a and 323b and test strip retainers 324a, 324b and 324c) presents a single analytical test strip 320 from a plurality of such analytical test strips in stacked configuration for engagement with extractor 307. In such a presentation, a portion of the top layer 321a and a portion of the bottom layer 321b of the single analytical test strip are splayed apart such that extractor 307, upon operative insertion into the test strip cartridge, is inserted between the splayed apart portion of the top layer and portion of the bottom layer (see FIG. 14B in particular). Extractor 307 includes two test strip engagement features 310a and 310b in the form of tabs.

Figure 14C:
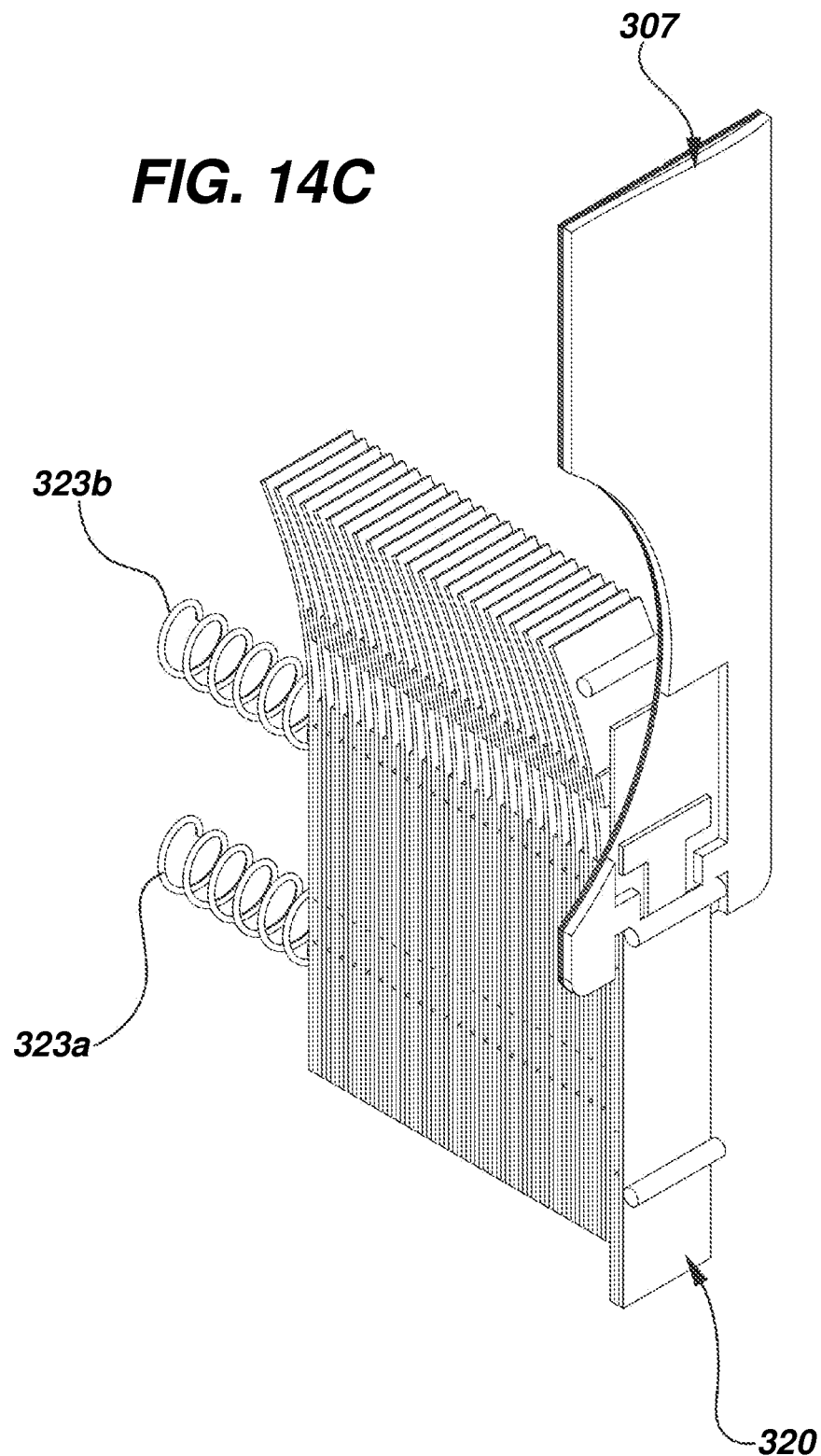

Further insertion of extractor 307 serves to push analytical test strip 320 downward and release bottom layer 321b from test strip retainer 324c (see FIG. 14C). As extractor 307 is retracted into a hand-held test meter (not shown) analytical test strip 320 is removed from the test strip presentation mechanism (see FIG. 14D).

FIGS. 15A and 15B illustrate the manner in which analytical test strip is mechanically engaged with extractor 307 via interlocking between test strip engagement features 310a and 310b and extractor engagement features 321a and 321b (see FIG. 15B in particular). Referring to FIGS. 15A and 15B, extractor 307 has two electrical contacts 352a and 352b on its rear side and a single electrical contact 352c on its front side. These electrical contacts make an electrical connection to two test strip electrical contacts on bottom layer 321b (not shown) and a single test strip electrical contact (not shown) on top layer 321a of analytical test strip 320.

Figure 16:
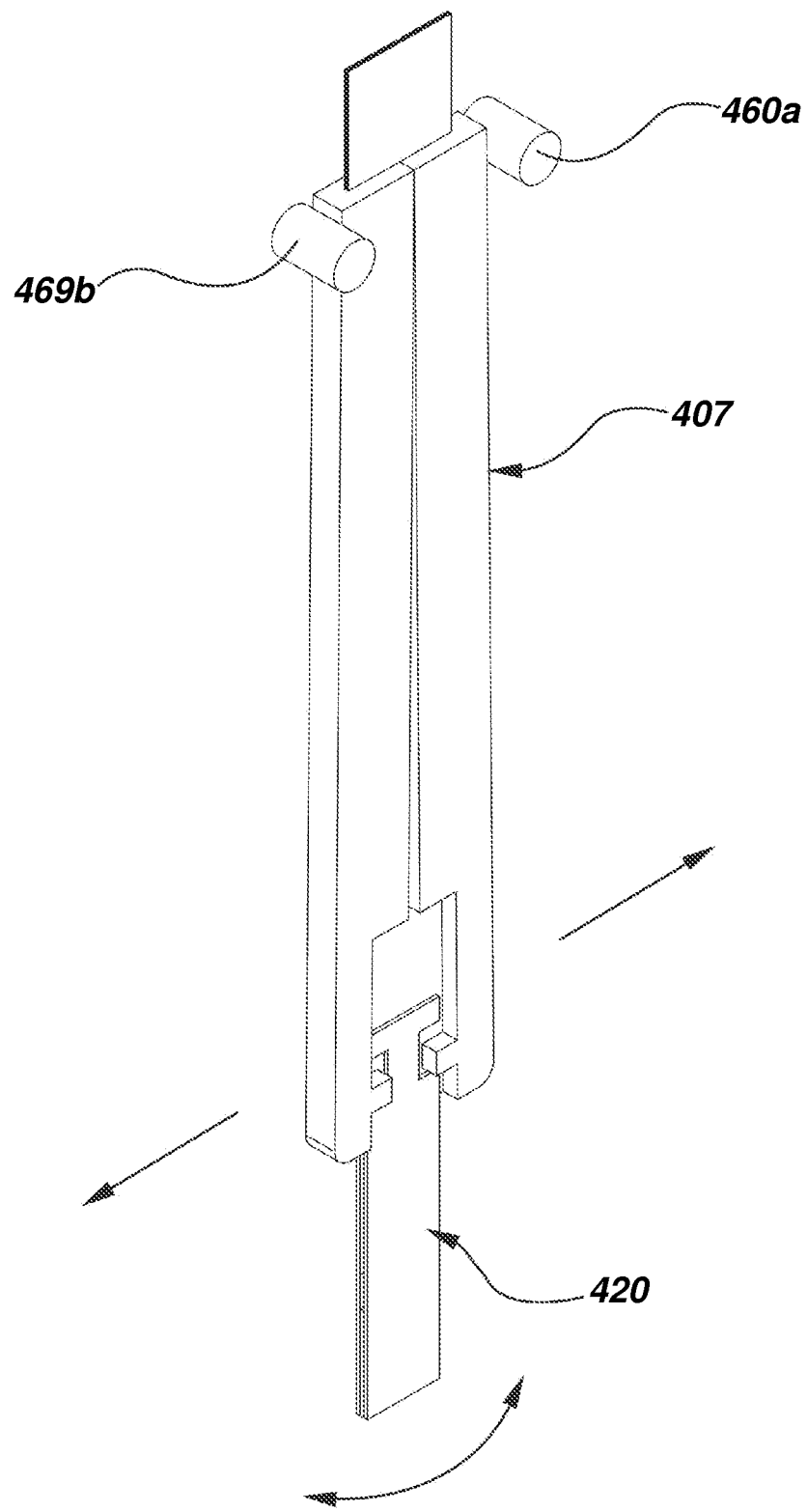
FIG. 16 is a simplified perspective depiction of an extractor and retainers of a hand-held test meter and an analytical test strip as can be employed in embodiments of the present invention with the extractor in an extended position.

FIG. 16 is a simplified perspective depiction of another extractor 407 and test strip retainers 460a and 460b of a hand-held test meter (not shown) and an analytical test strip 420 as can be employed in embodiments of the present invention with extractor 407 in an extended position and mechanically engaged with analytical test strip 420.

Extractor 407 is configured such that it spreads apart slightly (in the direction of the horizontal arrows in FIG. 16) when extended, as depicted by gap 470 in extractor 407. Such spreading provides a greater tolerance for engagement with analytical test strip 420 but also results in analytical test strip 420 being able to wobble in the direction of the curved double-headed arrow of FIG. 16. The spreading apart of extractor 407 can be accomplished by any suitable means including, for example, springs embedded within extractor 407.

Figure 17:
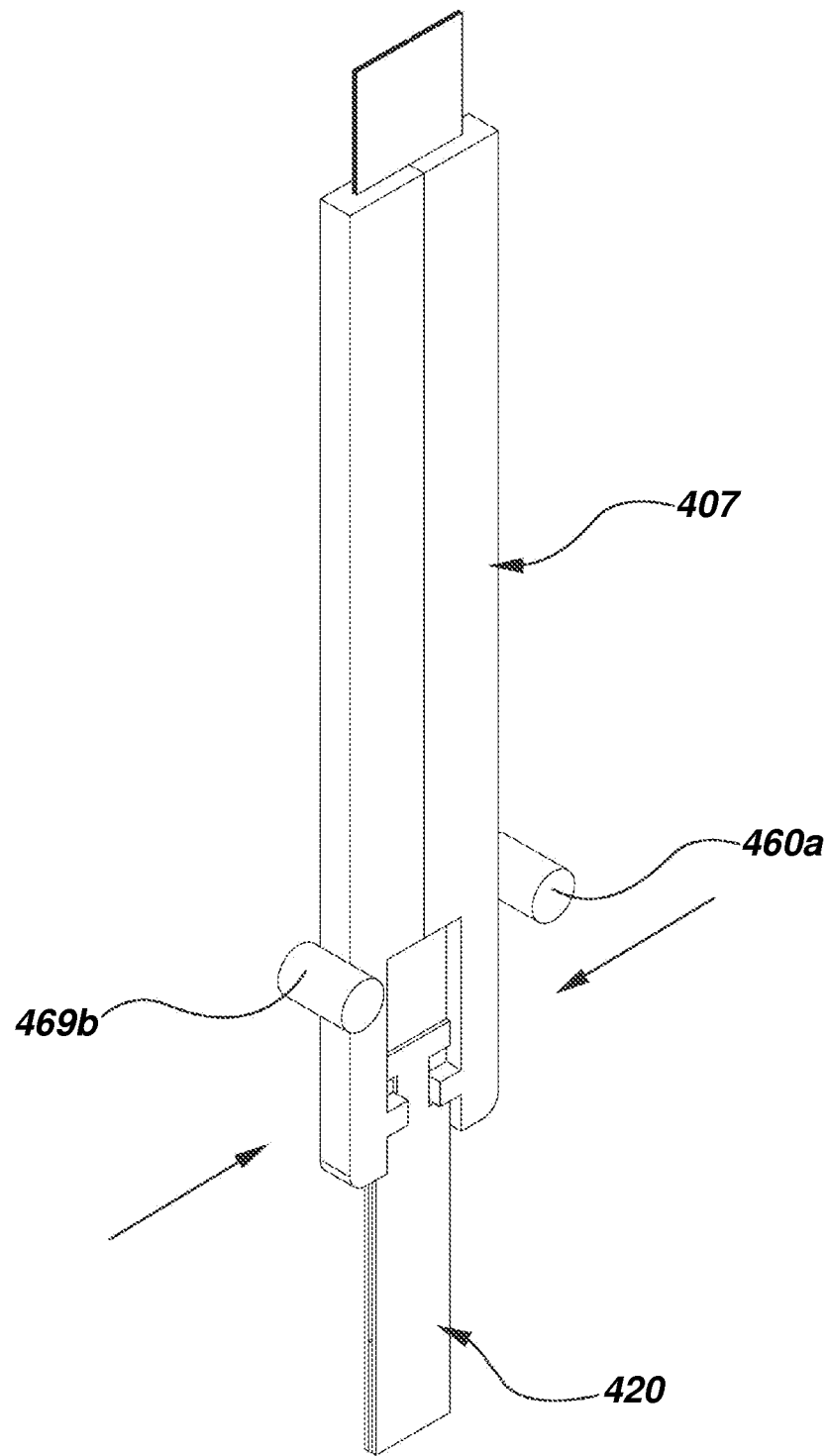
FIG. 17 is a simplified perspective depiction of an extractor and retainers of a hand-held test meter and an analytical test strip as can be employed in embodiments of the present invention with the extractor in a retracted position.

FIG. 17 is a simplified perspective depiction of extractor 407 in a retracted position that illustrates the manner in which test strip retainers 460a and 460b compress extractor 407 (in the direction of the horizontal arrows of FIG. 17) as extractor 407 is retracted (in the direction of the vertical arrow of FIG. 17), thus preventing further wobbling of analytical test strip 420.

Figure 18C:
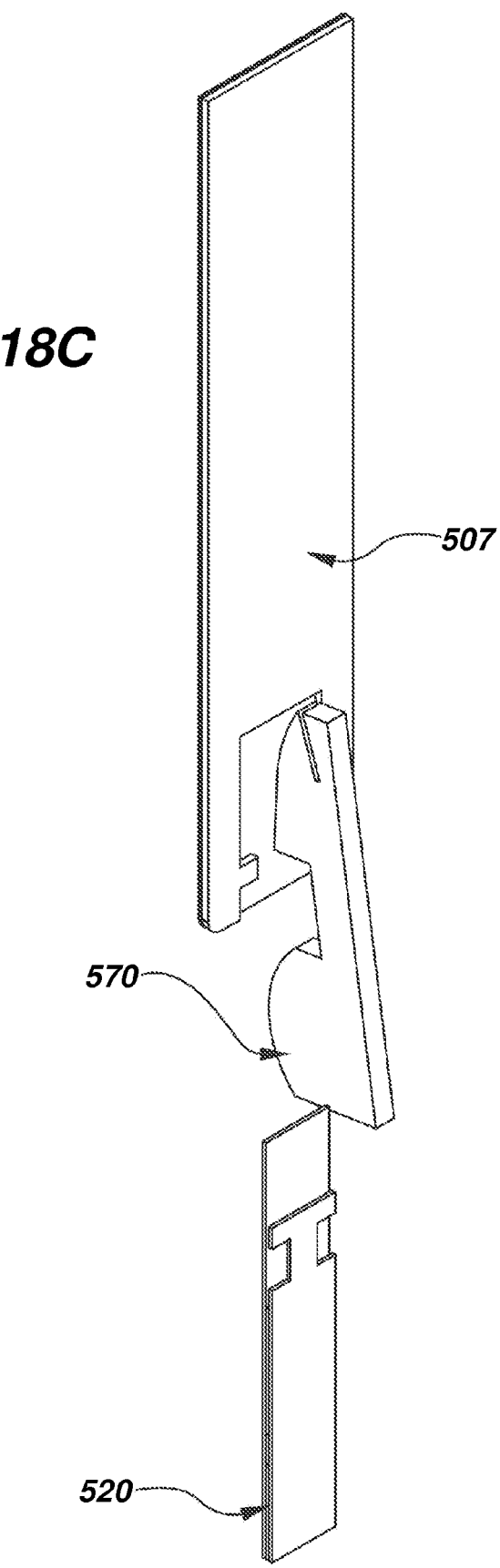

FIGS. 18A, 18B and 18C are a sequence of the simplified perspective drawings illustrating the operation of an extractor 507, analytical test strip 520 and analytical test strip release mechanism 570 according to an embodiment of the present invention. Analytical test strip mechanism 570 is a component of a hand-held test meter (not shown) and configured to slide along extractor 507 (in the direction of the downward arrows in FIGS. 18A and 18B) and apply a force against analytical test strip 520 (see the arrow marked F in FIG. 18B). The force serves to release the mechanical engagement between extractor 507 and analytical test strip 520 such that analytical test strip 520 falls free of extractor 507 (see FIG. 18C).

Figure 19:
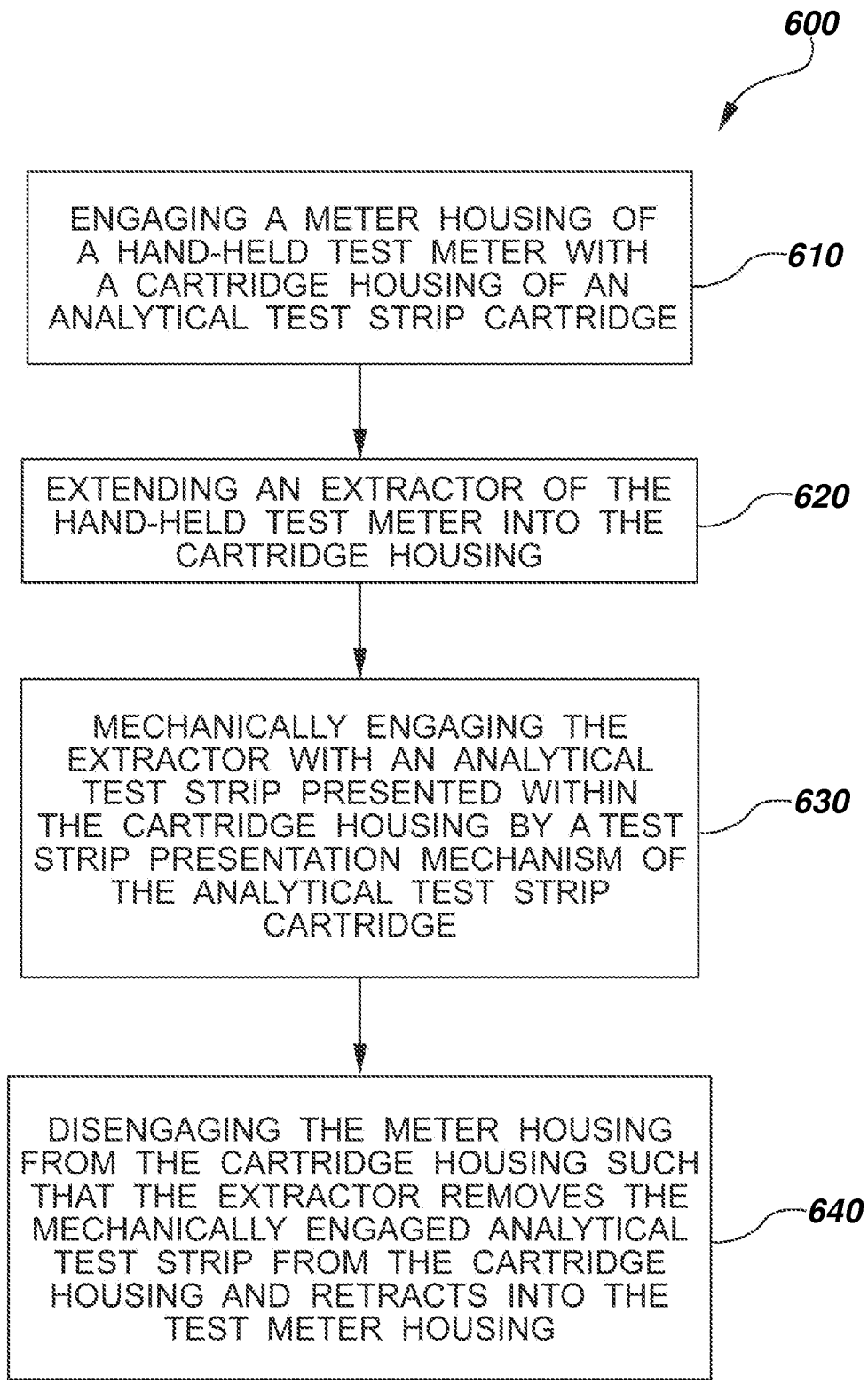
FIG. 19 is a flow diagram depicting stages in a method for employing a hand-held test meter according to an embodiment of the present invention.

FIG. 19 is a flow diagram depicting stages in a method 600 for employing a hand-held test meter and analytical test strip cartridge combination according to an embodiment of the present invention. Method 600 includes, at step 610, engaging a meter housing of a hand-held test meter with a cartridge housing of an analytical test strip cartridge and, at step 620, extending an extractor of the hand-held test meter into the cartridge housing.

Referring to step 630 of FIG. 19, the extractor is mechanically engaged with an analytical test strip disposed within the cartridge housing. In step 630, the analytical test strip is presented for mechanical engagement by a test strip presentation mechanism of the analytical test strip cartridge and the mechanical engagement occurring via engagement between a test strip engagement feature (such as, for example, a detent in the form of a spherical protrusion or one or more tabs) of the extractor and an extractor engagement feature (e.g., one or more notches) of the analytical test strip. Subsequently, the meter housing is disengaged from the cartridge housing such that the extractor removes the mechanically engaged analytical test strip from the cartridge housing and retracts into the test meter housing (see step 640 of method 600).

Once apprised of the present disclosure, one skilled in the art will recognize that methods according to embodiments of the present invention, including method 600, can be readily modified to incorporate any of the techniques, benefits and characteristics of hand-held test meter and analytical test strip cartridge combinations according to embodiments of the present invention and described herein.

In general, hand-held test meter and analytical test strip cartridge assembly combinations according to embodiments of the present invention include a hand-held test meter with a test meter housing and an extractor with a test strip engagement feature, while the analytical test strip cartridge assembly includes a desiccant vial and an analytical test strip cartridge. In addition, the analytical test strip cartridge includes a cartridge housing, a test strip presentation mechanism disposed within the cartridge housing, and a plurality of analytical test strips (e.g., a plurality of electrochemical-based analytical test strips) disposed in the cartridge housing. The test meter housing is configured for operative engagement with the cartridge housing and the test strip presentation mechanism is configured to present a single analytical test strip from the plurality of analytical test strips for engagement with the extractor. Moreover, the analytical test strip cartridge is configured for operative disposition in the desiccant vial.

Providing an analytical test strip cartridge that is also a sealed desiccated enclosure for analytical test strips within the cartridge is technically difficult and expensive. However, hand-held test meter and analytical test strip cartridge assembly combinations according to embodiments of the present invention are relatively inexpensive and employ a desiccated vial in conjunction with a test strip cartridge to provide a sealed desiccated enclosure for the analytical test strips.

Moreover, the test strip cartridge can be of technically simple on a relative basis since the test strip cartridge alone need not provide a sealed desiccated enclosure.

Referring to FIGS. 20 through 25, hand-held test meter and analytical test strip cartridge assembly combination 700 includes a hand-held test meter 702 and an analytical test strip cartridge assembly 704.

Hand-held test meter 702 includes a test meter housing 706 and an extractor (not depicted in FIGS. 20 through 25) with extractor electrical contacts and test strip engagement features (also not depicted in FIGS. 20 through 25). Hand-held test meter 702 also has a proximal end 712 and a distal end 714.

Once apprised of the present disclosure, one skilled in the art will recognize that hand-held test meter 702 includes suitable components for the determination of an analyte in a bodily sample applied to an analytical test strip engaged with the hand-held test meter's extractor. For the sake of simplicity and clarity, such suitable components are not depicted in the figures nor fully described herein. However, conventional hand-held test meters for the determination of an analyte in a bodily fluid sample are described in, for example, U.S. Pat. No. 7,468,125 and U.S. Patent Application Publication No.s 2009/0301899 and 2007/0084734, each of which is hereby incorporated in full by reference.

Analytical test strip cartridge assembly 704 includes a desiccant vial 716, and an analytical test strip cartridge 718. Analytical test strip cartridge 718 has a cartridge housing 720, a test strip presentation mechanism 722 disposed within cartridge housing 720 and a plurality of analytical test strips 724 disposed in cartridge housing 720, each of the analytical test strips having at least one extractor engagement feature (not depicted in FIGS. 20-25).

Once apprised of the present disclosure, one skilled in the art will recognize that the test strip presentation mechanism, plurality of analytical test strips, extractor, test strip engagement features, and extractor engagement features of hand-held test meter and analytical test strip cartridge assembly combinations according to embodiments of the present invention are essentially identical to the like-named components described elsewhere in this disclosure including, for example, with respect to FIGS. 1 through 19.

Cartridge housing 720 is formed as a single integrated unit and includes an air communication opening 726 configured for air communication between the plurality of analytical test strips 724 and desiccant vial 716. Cartridge housing 720 also includes a plurality of living hinges 728 that provide for cartridge housing to be manually placed into the opened state of FIG. 21, the opened state of FIG. 22 and the closed state of FIG. 23. In this regard, a living hinge is a thin flexible hinge made from the same material as the remainder of cartridge housing 720 with the remainder being relatively rigid.

Moreover, cartridge housing 720 includes a central cavity 730 (see FIG. 21) configured to hold a test strip presentation mechanism and a plurality of analytical test strips and also configured for the presentation of an analytical test strip to an extractor as described elsewhere herein. Cartridge housing 720 also includes a keyed opening 732 configured for operative engagement with hand-held test meter 702 in a single predefined orientation.

Cartridge housing 720 can be formed of any suitable material and by any suitable manufacturing techniques. Suitable materials include, but are not limited to polystyrene, polyethylene, high density polyethylene, and polyethylene terephthalate. Suitable manufacturing techniques include, but are not limited to, injection molding.

Figure 22:
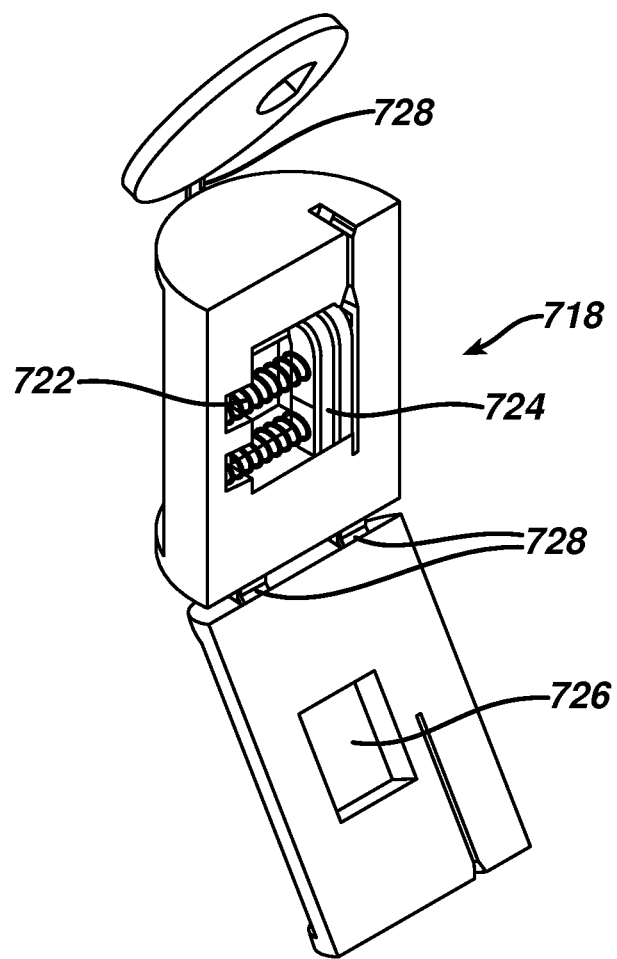
FIG. 22 is a perspective view of the cartridge housing of FIG. 21 in another opened state and loaded with a test strip presentation mechanism and a plurality of analytical test strips.

In hand-held test meter and analytical test strip cartridge assembly combination 700, test meter housing 706 is configured for operative engagement with cartridge housing 720 and test strip presentation mechanism 722 is configured to present a single analytical test strip from plurality of analytical test strips 724 for engagement with the hand-held test meter's extractor (see FIG. 22 in particular and refer to the related description of FIGS. 5A through 5C for further details).

Figure 20:
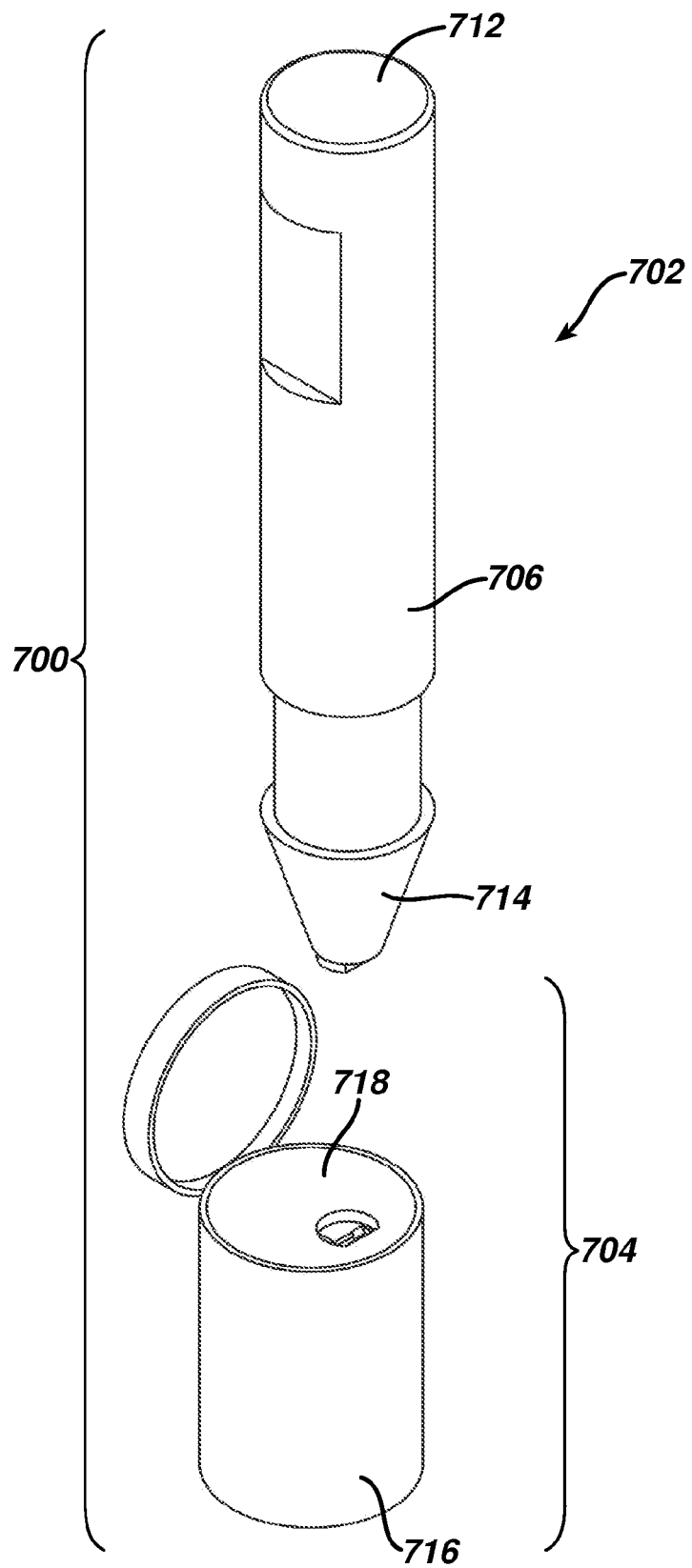
FIG. 20 is a simplified perspective depiction of a hand-held test meter and analytical test strip cartridge assembly combination according to an embodiment of the present invention.
Figure 21:
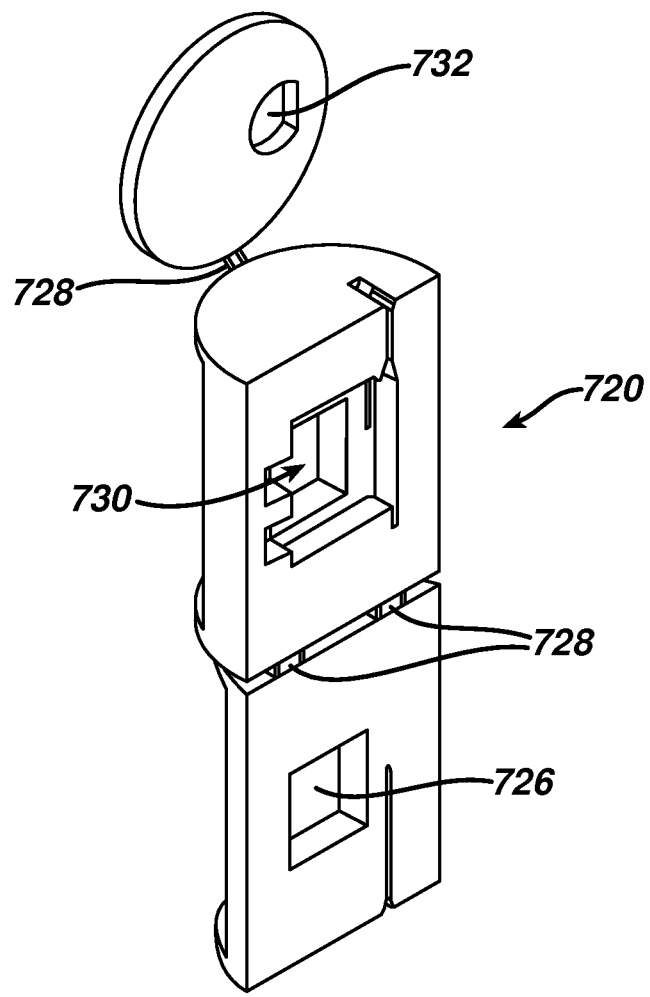
FIG. 21 is a simplified perspective view of an cartridge housing included in the analytical test strip cartridge assembly of FIG. 20 in an opened state.

Desiccant vial 716 can have any suitable configuration including, for example, the flip-top configuration depicted in FIGS. 20, 24, and 25. Desiccant vial includes a suitable desiccant material disposed therein by, for example, being integrally molded into the desiccant vial body and/or cap. Desiccant vial 716 is configured to provide a sealed desiccated enclosure for analytical test strip cartridge assembly 704 including, in particular, the plurality of analytical test strips 724 disposed within analytical test strip cartridge assembly 704.

Analytical test strip cartridge assembly 704 is configured for operative disposition in desiccant vial 716. In addition, as depicted in FIGS. 20 through 25, cartridge housing 720 is configured to accept a plurality of analytical test strips 724 and test strip presentation mechanism 722 when in an opened state (see FIGS. 21 and 22 in particular). Cartridge housing 720 can then manually placed into a closed state (see FIG. 23) that is configured for operative disposition within desiccant vial 716 (see FIGS. 20 and 25 in particular). A cartridge housing 720 in such a closed configuration can, for example, be manually disposed in a desiccant vial and securely held there by a snap or friction fit technique.

Once apprised of the present disclosure, one skilled in the art will recognize that hand-held test meter 702 will include such electronics and other components that are required or desired for the determination of an analyte (such as glucose) in a whole blood sample (such as a whole blood sample) applied to an analytical test strip after the analytical test strip has been extracted from analytical test strip cartridge assembly 704. However, such electronics and other components are not depicted in FIGS. 20 through 25 to avoid obscuring the beneficial features and functions of the present invention.

Hand-held test meter and analytical test strip cartridge assembly combinations according to embodiments of the present invention can be formed of any suitable materials known to one skilled in the art and manufactured using any suitable techniques.

Figure 26:
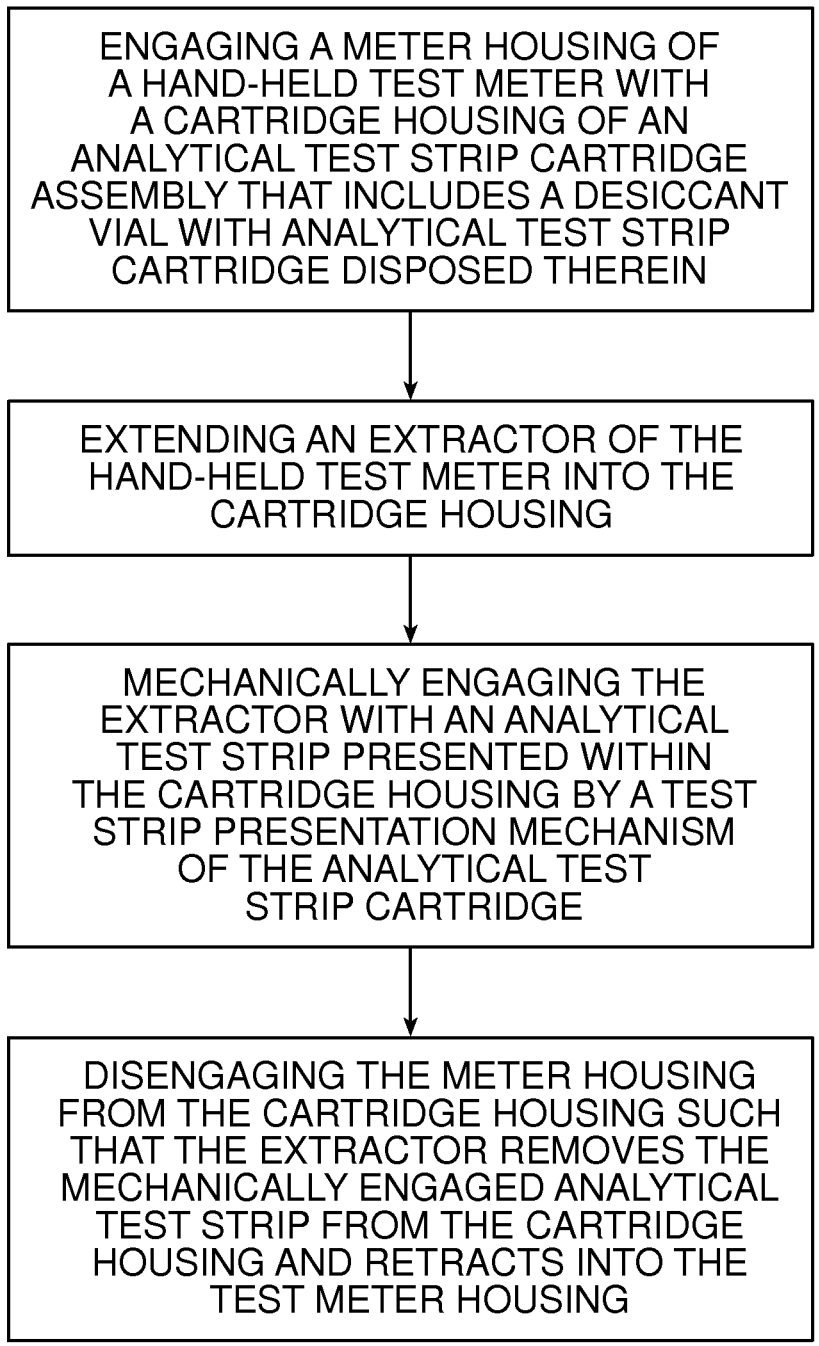
FIG. 26 is a flow diagram depicting stages in another method for employing a hand-held test meter according to an embodiment of the present invention.

FIG. 26 is a flow diagram depicting stages in a method 800 for employing a hand-held test meter and analytical test strip cartridge combination according to an embodiment of the present invention. Method 800 includes, at step 810, engaging a meter housing of a hand-held test meter with a cartridge housing of an analytical test strip cartridge assembly (e.g., the analytical test strip cartridge assembly described with respect to FIGS. 20 through 25) and, at step 820, extending an extractor of the hand-held test meter into the cartridge housing.

Referring to step 830 of FIG. 26, the extractor is mechanically engaged with an analytical test strip disposed within the cartridge housing. In step 830, the analytical test strip is presented for mechanical engagement by a test strip presentation mechanism of the analytical test strip cartridge and the mechanical engagement occurring via engagement between a test strip engagement feature (such as, for example, a detent in the form of a spherical protrusion or one or more tabs) of the extractor and an extractor engagement feature (e.g., one or more notches) of the analytical test strip. Subsequently, the meter housing is disengaged from the cartridge housing such that the extractor removes the mechanically engaged analytical test strip from the cartridge housing and retracts into the test meter housing (see step 840 of method 800).

Once apprised of the present disclosure, one skilled in the art will recognize that methods according to embodiments of the present invention, including method 800, can be readily modified to incorporate any of the techniques, benefits and characteristics of hand-held test meter and analytical test strip cartridge combinations and any techniques, benefits, and characteristics of hand-held test meter and analytical test strip assembly combinations according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A hand-held test meter and analytical test strip cartridge assembly combination comprising:
    a hand-held test meter including:
        a test meter housing; and
        an extractor with at least one test strip engagement feature; and
    an analytical test strip cartridge assembly including:
        a desiccant vial; and
        an analytical test strip cartridge including:
            a cartridge housing;
            a test strip presentation mechanism disposed within the cartridge housing, the test strip presentation mechanism comprising at least one test strip retainer; and
            a plurality of discrete analytical test strips disposed in the cartridge housing, each of the discrete analytical test strips having at least one extractor engagement feature and having a top layer and a bottom layer;
    wherein the test meter housing is configured for operative engagement with the cartridge housing; and
    wherein the test strip presentation mechanism is configured to present a single discrete analytical test strip from the plurality of discrete analytical test strips, and serves to splay part top and bottom layers of the single discrete analytical test strip, for engagement with the extractor; and
    wherein the analytical test strip cartridge is configured for operative disposition in the desiccant vial.

2. The hand-held test meter and analytical test strip cartridge assembly combination of claim 1 wherein the extractor and test meter housing are configured such that:
    the extractor is operatively extendable from the test meter housing into the cartridge housing upon engagement of the meter housing with the cartridge housing;
    the extractor, upon operative extension into the cartridge housing, mechanically engages with the discrete analytical test strip presented by the test strip presentation mechanism via engagement between the test strip engagement feature of the extractor and the extractor engagement feature of the discrete analytical test strip; and
    the extractor, upon disengagement of the test meter housing from the cartridge housing, removes the mechanically engaged discrete analytical test strip from the cartridge housing and retracts into the test meter housing.

3. The hand-held test meter and analytical test strip cartridge assembly combination of claim 1 wherein the desiccant vial includes a wall and a desiccant material molded into the wall.

4. The hand-held test meter and analytical test strip cartridge assembly combination of claim 1 wherein the cartridge housing includes an air communication opening configured for air communication between the plurality of discrete analytical test strips and the desiccant vial.

5. The hand-held test meter and analytical test strip cartridge assembly combination of claim 1 wherein the cartridge housing includes at least one living hinge.

6. The hand-held test meter and analytical test strip cartridge assembly combination of claim 1 wherein the cartridge housing includes a keyed opening; and
    wherein the test meter housing is configured for operative engagement with the keyed opening of the cartridge housing.

7. The hand-held test meter and analytical test strip cartridge assembly combination of claim 1 wherein the cartridge housing includes a center cavity configured for operative disposition of the plurality of discrete analytical test strips and the test strip presentation mechanism.

8. The hand-held test meter and analytical test strip cartridge assembly combination of claim 1 wherein the analytical test strip cartridge is configured for a press fit into the desiccant vial.

9. The hand-held test meter and analytical test strip cartridge assembly combination of claim 1 wherein the operative disposition of the analytical test strip cartridge in the desiccant vial provides a sealed desiccated enclosure for the discrete analytical test strips.

10. The hand-held test meter and analytical test strip cartridge assembly combination of claim 1 wherein the discrete analytical test strip is an electrochemical-based analytical test strip.

11. A method for employing a hand-held test meter and analytical test strip cartridge assembly combination, the method comprising:
    engaging a meter housing of a hand-held test meter with a cartridge housing of an analytical test strip cartridge assembly, the analytical test strip cartridge assembly including a desiccant vial with an analytical test strip cartridge disposed therein, the analytical test strip cartridge including a test strip presentation mechanism disposed therein, the test strip presentation mechanism splaying apart top and bottom layers of an analytical test strip disposed within the cartridge housing;
    extending an extractor of the hand-held test meter into the cartridge housing;
    mechanically engaging the extractor with splayed analytical test strip being presented for mechanical engagement by the test strip presentation mechanism of the analytical test strip cartridge and with the mechanical engagement occurring via engagement between a test strip engagement feature of the extractor and an extractor engagement feature of the discrete analytical test strip; and
    disengaging the meter housing from the cartridge housing such that the extractor removes the mechanically engaged discrete analytical test strip from the cartridge housing and retracts into the test meter housing.

12. The method of claim 11 further comprising:

determining an analyte in a bodily fluid sample applied to the mechanically engaged discrete analytical test strip; and releasing the discrete analytical test strip from the mechanical engagement with the extractor using a test strip release mechanism of the hand-held test meter.

13. The method of claim 12 wherein the bodily fluid sample is a whole blood sample and the analyte is glucose.

14. The method of claim 11 wherein the discrete analytical test strip being presented is being presented from among a plurality of discrete analytical test strips disposed within the analytical test strip cartridge assembly.

15. The method of claim 11 wherein the desiccant vial includes a wall and a desiccant material molded into the wall.

16. The method of claim 11 wherein the cartridge housing includes an air communication opening configured for air communication between the plurality of discrete analytical test strips and the desiccant vial.

17. The method of claim 11 wherein the cartridge housing includes at least one living hinge.

18. The method of claim 11 wherein the cartridge housing includes a keyed opening; and wherein the test meter housing is configured for operative engagement with the keyed opening of the cartridge housing.

19. The method of claim 11 wherein the cartridge housing includes a center cavity configured for operative disposition of the plurality of discrete analytical test strips and the test strip presentation mechanism.

20. The method of claim 11 wherein the analytical test strip cartridge is configured for a press fit into the desiccant vial.

21. The method of claim 11 wherein the operative disposition of the analytical test strip cartridge in the desiccant vial provides a sealed desiccated enclosure for the discrete analytical test strips.

* * * * *